US005081131A

United States Patent [19]

Tomcufcik et al.

[11] Patent Number: 5,081,131

[45] Date of Patent: Jan. 14, 1992

[54] OMEGA-((HETERO)ALKYL)BENZ(CD)-INDOL-2-AMINES

[75] Inventors: Andrew S. Tomcufcik, Bergen, N.J.; Walter E. Meyer; Peter S. Chan, both Suffern, N.Y.; David L. Crandall, Highland Mills, N.Y.

[73] Assignee: American Cyanamid Company, Stamford, Conn.

[21] Appl. No.: 225,972

[22] Filed: Jul. 29, 1988

Related U.S. Application Data

[63] Continuation of Ser. No. 199,617, May 27, 1988, abandoned, which is a continuation-in-part of Ser. No. 937,848, Dec. 11, 1986, abandoned, which is a continuation-in-part of Ser. No. 818,315, Jan. 13, 1986, Pat. No. 4,728,663.

[51] Int. Cl.[5] .................... A61K 31/44; C07D 401/00; C07D 413/00

[52] U.S. Cl. .................................... 514/339; 546/256; 546/15; 546/272; 514/333

[58] Field of Search ......................... 546/256, 272, 15; 514/333, 339

[56] References Cited

U.S. PATENT DOCUMENTS 4,529,804 7/1985 Frey et al. .......................... 546/256
4,569,942 2/1986 Kadin ................................ 546/256

FOREIGN PATENT DOCUMENTS 870185 7/1988 South Africa ...................... 546/256

*Primary Examiner*—Mary C. Lee
*Assistant Examiner*—Robert C. Whittenbaugh
*Attorney, Agent, or Firm*—Robert P. Raymond

[57] ABSTRACT

Omega-((hetero)alkyl)benz(cd)indol-2-amines useful in inhibition of thromboxane synthetase and in treatment of hypertension in warm-blooded animals are disclosed.

12 Claims, No Drawings

OMEGA-((HETERO)ALKYL)BENZ(CD)-INDOL-2-AMINES

SUMMARY OF THE INVENTION

This application is a continuation of Ser. No. 07/199,617 filed May 27, 1988, now abandoned, which is a continuation-in-part of application Ser. No. 937,848, filed Dec. 11, 1986, now abandoned, which is in turn a continuation-in-part of Ser. No. 818,315, filed Jan. 13, 1986, now U.S. Pat. No. 4,728,663.

This invention relates to new organic compounds and, more particularly, is concerned with novel substituted and unsubstituted omega-((hetero)alkyl)benz(c-d)indol-2-amines which may be represented by the structural formula:

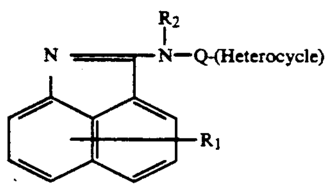

wherein $R_1$ is selected from the group of one or more of the following: bromo, chloro, fluoro, iodo, loweralkyloxy, loweralkylthio, lower alkylsulfonyl, arylsulfonyl, hydroxy, mercapto, loweralkylcarbonyloxy, amino, mono(loweralkyl)amino, di(loweralkyl)amino, alpha, omega-alkylene)amino, loweralkyl, aryl(loweralkyl), cycloalkyl, lowercycloalkyloxy, loweralkylcarbonyl, arylcarbonyl, cyano, sulfonamido, N-(loweralklyl)-sulfonamido, N,N-(diloweralkyl)sulfonamido, alpha-hydroxy(lower)alkyl, alpha-amino(loweralkyl), alpha-(loweralkyl)amino(loweralkyl), alpha-(diloweralkyl-)amino(loweralkyl), carboxamido, N-(loweralkyl)carboxamido, N,N-(diloweralkyl)carboxamido, the remaining positions in the napthalene ring being occupied by hydrogen; where $R_2$ is selected from the group consisting of hydrogen, alkyl($C_1$–$C_8$), aryl, arylakyl, cycloalkyl, alkyl($C_1$–$C_6$)carbonyl, (substituted aryl)carbonyl, furancarbonyl, thiophenecarbonyl, pyridinecarbonyl, arylsulfonyl, and arylaminocarbonyl; where Q is selected from the group consisting of $(CH_2)_n$ where n is an integer from 1 to 12, where such chain is substituted by one or more lower alkyl, cycloalkyl, arylalkyl, aryl, spiroalkyl, hydroxy, loweralkoxy, fluoro, and where such chain contains one or more —CH═CH— or —C≡C— linkages, where the chain may also be cyclohexane(bisalkyl), and where such chain may have functions such as —O—, —S—, —$SO_2$—, —NH—, $$\begin{array}{c} R_3 \\ | \\ -N- \end{array}$$

(where $R_3$ is H, alkyl ($C_1$–$C_8$), aryl, arylalkyl or cycloalkyl), and $$\begin{array}{c} O \\ \| \\ -C-NH \end{array}$$

replacing one of the —$CH_2$— groups; where (heterocycle) represents unsubstituted or substituted 1H-imidazol-1-yl, 1H-imidazol-4-yl, 2-, 3-, and 4-pyridyl, benzimidazol-1-yl, 1H-indol-1-yl, 1H-indazol-1-yl, 1H-benzotriazol-1-yl, 1H-pyrazol-1-yl, 1H-1,2,3-triazol-1-yl, 1H-1,2,4-triazol-1-yl, 2H-1,2,3-triazol-4-yl, 2-thiazolyl, 2-furanyl, 2-thiophenyl, pyrimidinyl, quinolinyl, 1,3,4-thiadiazol-2-yl, 2-pyrazinyl, 3- and 4-pyridazinyl, 1- and 2-pyrrol-1-yl or the like; and the pharmacologically acceptable salts thereof.

As used herein, the term "lower alkyl" denotes a straight or branched chain saturated hydrocarbon containing 1 to 8 carbon atoms, for example, methyl, ethyl, propyl, isopropyl, butyl, t-butyl, neopentyl, pentyl, heptyl and the like. The term "alkylene" denotes a hydrocarbon radical of 2 to 8 carbon atoms, preferably of 4 to 6 carbon atoms, such as ethylene, propylene, butylene and pentylene, which may be substituted by one or more lower alkyl groups, for example, 1 methyl-propylene, 1-methyl-butylene or the like. The term "lower alkoxy" denotes an alkyl ether group in which the lower alkyl group is as described above, for example, methoxy, ethoxy, propoxy, pentoxy and the like. The term "halogen" denotes all halogens, that is, bromine, chlorine, fluorine and iodine. The term "aryl") denotes 1-naphthyl, 2-naphthyl, diphenylmethyl, 9-fluorenyl or a moiety of the formula:

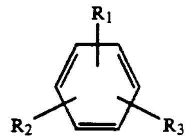

wherein $R_1$, $R_2$ and $R_3$ are each individually selected from the group consisting of hydrogen, halogen, trifluoromethyl, cyano, carboxy, amino, alkyl having from one to four carbon atoms, alkoxy having from one to four carbon atoms, benzylamino, allylamino, alkylamino having from one to three carbon atoms, dialkylamino having from one to three carbon atoms in each alkyl group, alkylthio having from one to three carbon atoms, alkylsulfonyl having from one to three carbon atoms, acetyl, acetamido, phenyl and benzoyl.

The term cycloalkyl denotes aliphatic cyclic hydrocarbons containing from 3 to 10 carbon atoms, namely cyclopropane, cyclobutane, cyclopentane, cyclohexane and the like, unsubstituted or substituted with substituents selected from the group consisting of hydrogen, halogen, trifluoromethyl, cyano, carboxy, amino, alkyl having from one to four carbon atoms, benzylamino, allylamino, alkylamino having from one to three carbon atoms, dialkylamino having from one to three carbon atoms in each alkyl group, alkylthio having from one to three carbon atoms, alkylsulfonyl having from one to three carbon atoms, acetyl, acetamido, phenyl and benzoyl. The term spiroalkyl denotes 2,2-spiro-pentamethylene and the like.

The term heterocycle denotes an unsubstituted or substituted 5- or 6-membered heterocyclic ring, which may be fused to another 6-membered heterocyclic or non-heterocyclic ring, especially heteroaromatic rings which contain 1 to 3, or particularly 1 or 2, heteroatoms which may be the same or different. Nitrogen, oxygen and sulfur are the preferred heteroatoms. A substituted heterocyclic group may be substituted by one or more, preferably 1 or 2, substituents which may be the same or different. Preferred substituents are straight and branched-chain lower alkyl, especially of 1 or 2 carbon atoms; straight- and branched-chain lower alkoxy, especially of 1 or 2 carbon atoms; halogen; and nitro.

The above-mentioned substituents may be varied in regard to their degree of saturation. For example, it is contemplated that the term "lower alkyl" includes double and triple bonded carbon chains of 2 to 8 carbon atoms, such as butenyl, pentyl, butynyl and pentynyl and the like. Similarly, the term cycloalkyl includes cyclobutenyl, cyclopentyl, cyclobutynyl, cyclopentynyl and the like.

The organic bases of this invention form non-toxic acid-addition salts with a variety of pharmacologically acceptable organic and inorganic salt-forming reagents. Thus acid-addition salts, formed by admixture of the organic free base with one or more equivalents of an acid, suitably in a neutral solvent, are formed with such acids as sulfuric, phosphoric, hydrochloric, hydrobromic, hydroiodic, sulfamic, citric, lactic, malic, succinic, maleic, fumaric, tartaric, acetic, benzoic, fluconic, ascorbic and the like. For the purpose of this invention the free bases are equivalent to their non-toxic acid addition salts.

DETAILED DESCRIPTION OF THE INVENTION

The compounds of the present invention may be readily prepared according to the following reaction schemes, wherein $R_1$, $R_2$, $R_3$, Q, and (Heterocycle) are as described hereinabove.

Scheme 1:

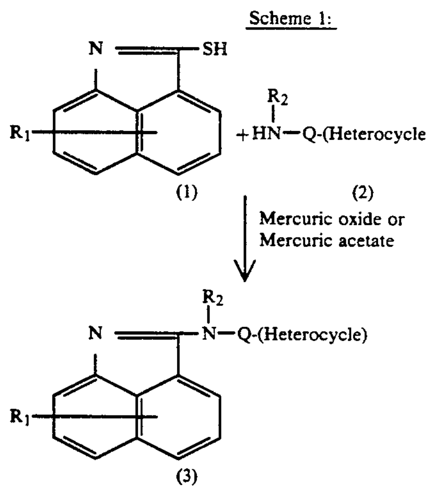

In accordance with the above reaction scheme a substituted benz(cd)indol-2-thiol (1) is reacted with an amine of the general structure (2) and mercuric oxide or mercuric acetate in a suitable solvent such as ethanol, butanol, or 2-methoxyethanol at reflux temperature for several hours, giving the desired compounds.

The compounds of Structure (1) are readily prepared by the following reaction:

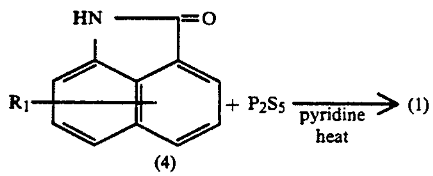

Compounds of Structure (4) are well known in the literature, and are prepared as shown in Great Britain Patent 1,595,050, U.S. Pat. No. 2,628,964, West Germany Patent DE 3,443,994, *Helv. Chim. Acta* 34 382 (1951), *J. Org. Chem. USSR* 7 150 (1971) and 8 826 (1972), and others. The conversion of compounds of Structure (4) to those of Structure (1) is readily accomplished as described in the *J. Gen. Chem. USSR* 24 1871 (1954).

The compounds of Structure (2) are also well known in the literature and are prepared by the methods and procedures as exemplified in U.S. Pat. Nos. 4,551,460 and 4,568,687, *Helv. Chim. Acta* 65 1868 (1982), *J. Het. Chem.* 10 30 (1973), *Eur. J. Med. Chem. Chim. Ther.* 1985-20 (S) p. 403, and *J. Med. Chem.* 29 2280 (1986), and others.

Scheme 2:

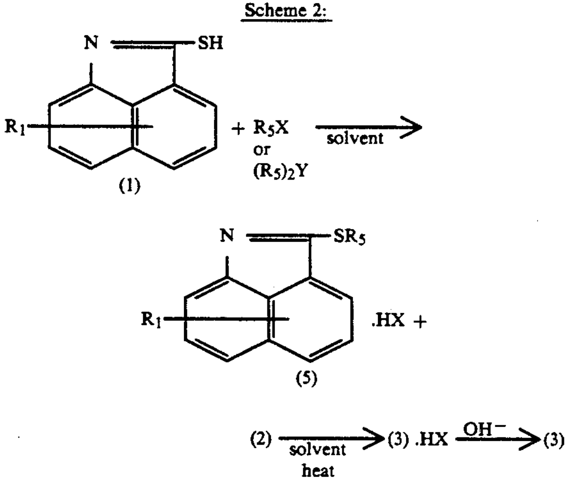

In accordance with the above scheme, a benz(cd) indol-2-thiol derivative of Structure (1) is dissolved in a solvent such as acetone, ethanol and the like and treated with a slight excess of an alkylating agent $R_5X$ or $(R_5)_2Y$ (where $R_5$ is alkyl or arylalkyl; X is halo; and Y is sulfate), such a iodomethane, bromoethane, dimethyl sulfate, benzylchloride and the like, yielding a 2-substituted thiobenz(cd)indole salt (Structure 5), as discussed in *J. Chem. Soc.* 1960 1537. The latter compounds when treated with the amines of Structure (2) in an appropriate solvent such as ethanol, 2-methoxyethanol, etc. yield the HX salts of the compounds of Structure (3) which when neutralized with alkali hydroxides yield the free bases (Structure (3)).

Scheme 3:

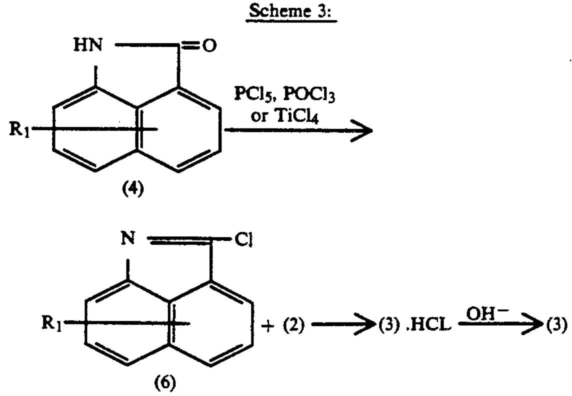

By this reaction scheme, compounds of Structure (4) when treated with $PCl_5$, $POCl_3$, $TiCl_4$, and the like in a suitable solvent can yield a 2-chlorobenz(cd)indole of Structure (6), which upon treatment with (2), followed by treatment with alkali hydroxides can yield the free base (Structure (3)).

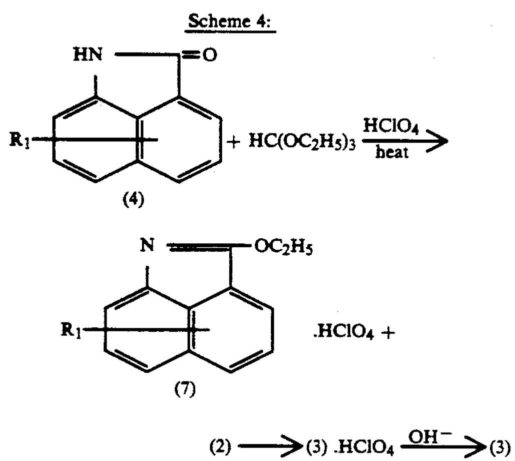

According to this reaction scheme, compounds of Structure (4) when treated with triethylorthoformate in the presence of perchloric acid can yield 2-ethoxybenz(cd)indole perchlorate salts of Structure (7) which when treated with compounds of Structure (2) can yield the perchlorate salts of compounds of Structure (3), which on treatment with alkali hydroxide can give the compounds of Structure (3). The reaction of (4) with triethylorthoformate in the presence of perchloric acid is exemplified in *J. Org. Chem. USSR* 17 (10) 2225 (1981).

The compounds of this invention inhibit thromboxane synthetase enzyme. Thus, these compounds are useful in the treatment of disease characterized by an imbalance of thromboxane $A_2$/prostacyclin such as ischemic heart disease, transient ischemic attack, thrombosis and migraine. Recent reviews have established the role of the thromboxane/prostacyclin balance in the vascular system (*Cardiovascular Diseases: New Trends in Surgical and Medical Aspects,* H. Barnet, P. Paoletti, E. Flamm and G. Brambilla, eds., Elsevier/North Holland Biomedical Press, pp 137–150 (1982)). Prostacyclin ($PGI_2$) is a potent vasodilator and platelet aggregation inhibitor, whereas thromboxane ($TXA_2$) is a powerful vasoconstrictor and causative of platelet aggregation. $TXA_2$ is synthesized by thromboxane synthetase enzyme located in, for example, blood platelets. When $TXA_2$ production is increased relative to $PGI_2$, platelet aggregation, thrombosis and vasospasm may occur (Lancet (i), 1216 (1977); *Lancet,* 479 (1977); *Science,* 1135 (1976); *Amer. J. Cardiology,* 41 787 (1978)). $TXA_2$ synthetase inhibitors have been shown to have superior anti-thrombotic action to that of aspirin (*J. Clin. Invest.,* 65 400 (1980); *Br. J. Pharmac.,* 76, 3 (1982)).

The role of prostagladins including $TXA_2$ and $PGI_2$ in ischemic heart patients has been reviewed (*Cardiovascular Pharmacology of the Prostagladins,* A. G. Herman, P. M. Vanhoute, H. Denolin and A. Goosens, eds., Raven Press, New York, pp 361–374 (1982)). Injection of $TXA_2$ into coronary arteries of guinea pigs and rabbits causes myocardial ischemia and subendocardial necrosis (*Drugs of the Future,* 7, 331 (1982); *Proc. Jap. Acad.,* 53(B), 38 (1977); *Eur. J. Pharmacol.,* 53 49 (1978)). Recent research has demonstrated the beneficial effects of $PGI_2$ and selective inhibition of thromboxane synthetase on ischemic myocardium in canines (J. Cardiovascular Pharmacology, 4, 129 (1982)). Thus compounds which selectively inhibit thromboxane synthetase (and hence $TXA_2$) without adversely affecting $PGI_2$ are useful in the treatment of vascular diseases such as ischemia and migraine. In addition, inhibition of $TXA_2$ formation may effectively treat platelet aggregation and prevent thrombosis.

Under urethan anesthesia, (1 g/kg i.p.), 9.0 ml of arterial blood was collected through a cannula inserted into the carotid artery in 1 ml of 3.2% sodium citrate into a polystyrene tube from a male Okamoto-Aoki spontaneously hypertensive rat (Taconic Farms, Germantown, N.Y.) between 19 and 24 weeks of age. The blood was diluted with 3 ml cold saline and centrifuged at room temperature for 15 min at $468\times g$. The platelet rich plasma (PRP) was separated. The platelets were isolated by certrifuging the PRP for 10 minutes at $1060\times g$ and washed in 4 ml cold oxygenated Krebs phosphate buffer, pH 7.4. The chilled platelets recovered from centrifuging at $800\times g$ for 10 minutes were resuspended in oxygenated Krebs phosphate buffer and diluted to contain $4.0–6.0\times10^4$ platelets/micro-liters.

The inhibition of TX formation was studied by determining the concentration of thromboxane $B_2$ ($TXB_2$), the stable hydrolysis product of $TXA_2$. Assay samples prepared on ice, contained 200 micro-liters platelet suspension, 50 micro-liters saline, and 50 micro-liters vechicle (saline) or drug under study. The test drug (0.003 mole) was dissolved in 5 ml of saline. Serial dilutions of the test drug solution were made with 0.9% saline to give assay concentrations of $1\times10^{-4}$ to $1\times10^{-9}$ mole.

The assay samples were incubated for 10 minutes at 37° C. in a metabolic shaker at about 60 rpm. The reaction was terminated by immersing the tubes in an ice bath and adding 50 micro-liters of 0.5M citric acid. The samples were centrifuged for 10 minutes at 2000 rpm at 4° C., and the supernatants were decanted. The $TXB_2$ content in each sample was determined by a direct radioimmunoassay (RIA) utilizing a $TBX_2$ specific RIA kit purchased from the New England Nuclear, Boston, Mass., and expressed as pg $TXB_2$ formed minute$^{-1}$, sample$^{-1}$, from which the percent inhibition of $TXB_2$ formation was calculated.

Table I shows the percentage of thromboxane synthetase enzyme inhibition when the compound was employed at an assay concentration of $1\times10^{-4}$ Molar.

TABLE I

Thromboxane Synthetase Enzyme Inhibition

| Compound | % Inhibition |
|---|---|
| N-(3-(1H-imidazol-1-yl)propyl)benz(cd)-indol-2-amine, dihydrochloride | 85 |
| 6-Bromo-N-(3-H-imidazol-1-yl)propyl)-benz(cd)indol-2-amine, dihydrochloride | 85 |
| N-[3-(1H-imidazol-1-yl)butyl)benz(cd)-indol-2-amine, dihydrochloride | 92 |
| N-(1-(4-chlorophenyl)-2-(1H-imidazol-1-yl)ethyl)benz(cd)indol-2-amine, fumarate | 35 |
| N-(3-(1H-imidazol-1-yl)-2-methylpropyl)-benz(cd)indol-2-amine, dihydrochloride | 95 |
| N-(3-(1H-imidazol-1-yl)-1-phenylpropyl)-benz(cd)indol-2-amine, fumarate | 100 |
| N-(3-(1H-imidazol-1-yl)-2-methylpropyl)-benz(cd)indol-2-amine, fumarate | 100 |
| N-(5-(1H-imidazol-1-yl)pentyl)benz(cd)-indol-2-amine, fumarate | 95 |

TABLE I-continued

| Thromboxane Synthetase Enzyme Inhibition | |
|---|---|
| Compound | % Inhibition |
| (Z)-N-(4-(1H-imidazol-1-yl)-2-butenyl)-benz(cd)indol-2-amine, dihydrochloride | 97 |
| N-(3-(2-Phenyl-1H-imidazol-1-yl)propyl)-benz(cd)indol-2-amine, hydriodide | 100 |
| N-(3-(2-Methyl-1H-imidazol-1-yl)propyl)-benz(cd)indol-2-mine, hydriodide | 82 |
| N-(4-(1H-imidazol-1-yl)butyl)benz(cd)-indol-2-amine, hydriodide | 100 |
| (Z)-N-(4-(1H-imidazol-1-yl)-2-butenyl)-benz(cd)indol-2-amine, hydriodide | 100 |
| (E)-N-(4-(1H-imidazol-1-yl)-2-butenyl)-benz(cd)indol-2-amine, hydriodide | 100 |
| N-(3-(1H-benzimidazol-1-yl)propyl)benz-(cd)indol-2-amine, fumarate | 90 |
| N-(3-(1H-benzimidazol-1-yl)propyl)benz-(cd)indol-2-amine | 60 |
| N-(4-(1H-imidazol-1-yl)butyl)benz(cd)-ndol-2-amine, fumarate | 100 |
| N-(5-(1H-imidazol-1-yl)-3-methylpentyl)-benz(cd)indol-2-amine,dihydrochloride | 100 |
| N-(10-(1H-imidazol-1-yl)decyl)benz(cd)-indol-2-amine, fumarate | 65 |
| N-(2-(1H-imidazol-1-yl)ethyl)benz(cd)-indol-2-amine | 71 |
| 6-Bromo-N-(3-(1H-imidazol-1-yl)butyl)-benz(cd)indol-2-amine | 100 |
| N,N-Dimethyl-2-((3-(1H-imidazol-1-yl)-butyl)amino)benz(cd)indol-6-sulfonamide | 99 |
| N,N-Dimethyl-2-((3-(1H-imidazol-1-yl)-propyl)amino)benz(cd)indol-6-sulfonamide | 100 |
| 6-Bromo-N-(10-(1H-imidazol-1-yl)decyl)-benz(cd)indol-2-amine | 94 |
| 6-Bromo-N-(4-(1H-imidazol-1-yl)butyl)-benz(cd)indol-2-amine | 98 |
| 2-(Benz(cd)indol-2-ylamino)-N-(3-(1H-imidazol-1-yl)propyl)acetamide | 100 |
| N-((4-(1H-imidazol-1-ylmethyl)phenyl)-methyl)benz(cd)indol-2-amine, fumarate | 100 |
| 6,8-Dichloro-N-(10-(1H-imidazol-1-yl)-decyl)benz(cd)indol-2-amine | 96 |
| 6,8-Dichloro-N-(3-(1H-imidazol-1-yl)-propyl)benz(cd)indol-2-amine | 97 |
| 6-Bromo-N-(5-(1H-imidazol-1-yl)pentyl)-benz(cd)indol-2-amine | 97 |
| 6-Chloro-N-(5-(1H-imidazol-1-yl)-pentyl)benz(cd)indol-2-amine | 100 |
| N-(4-(1H-imidazol-1-yl)pentyl)benz-(cd)indol-2-amine, fumarate | 99 |
| 6-Chloro-N-(4-(1H-imidazol-1-yl)butyl)-benz(cd)indol-2-amine, fumarate | 100 |
| N-(3-(1H-imidazol-1-yl)-2, 2-diphenyl-propyl)benz(cd)indol-2-amine | 75 |
| N-(2-(2-(1H-imidazol-1-yl)ethoxy)-ethyl)benz(cd)indol-2-amine bis-fumarate | 98 |
| N-(8-(1H-imidazol-1-yl)octyl)benz(cd)-indol-2-amine dihydrochloride | 100 |
| N-(4-(1H-imidazol-1-yl)pentyl)benz (cd)indol-2-amine, bis-fumarate | 99 |
| 6,8-Dichloro-N-(4-(1H-imidazol-1-yl)-butyl)benz(cd)indol-2-amine | 99 |
| N-(3-(1H-imidazol-1-yl)propyl)benz-(cd)indol-2-amine, fumarate | 92 |
| N-(12-(1H-imidazol-1-yl)dodecyl)-benz(cd)indol-2-amine | 97 |
| 6-Bromo-N-(12-(1H-imidazol-1-yl) dodecyl)benz(cd)indol-2-amine | 90 |
| N-Benz(cd)indol-2-yl-N-(4-(1H-imidazol-1-yl)butyl)acetamide | 98.5 |
| N-Benz(cd)indol-2-yl-N-(3-(1H-imidazol-1-yl)propylbenzamide | 94.5 |
| N-Benz(cd)indol-2-yl-N-(3-(1H-imidazol-1-yl)propyl)benzenesulfonamide | 93 |
| N-Benz(cd)indol-2-yl-N-(3-(1H-imidazol-1-yl)butyl)propionamide | 95 |
| N-Benz(cd)indol-2-yl-4-chloro-N-(4-(1H-imidazol-1-yl)butylbenzamide | 96 |
| N-(2-(4-(1H-imidazol-1-yl)butyl(benz-(cd)indol-6-yl)-4-methylbenzene-sulfonamide monoacetate | 79 |
| N-(3-(1H-imidazol-1-yl)-2-hydroxy-propyl)benz(cd)indol-2-amine | 88 |
| N-Benz(cd)indol-2-yl-N-(4-(1H-imidazol-1-yl)butyl)-2-methoxybenzamide | 93 |
| N-(2-(3-Pyridinyl)ethyl)benz(cd)-idol-2-amine, sesqui-fumarate | 99 |
| N-(2-(2-Pyridinyloxy)ethyl)benz(cd)-indol-2-amine, fumarate | 88 |
| N-(3-Pyridinylmethyl)benz(cd)indol-2-amine, fumarate | 68 |
| N-(2-Pyridinylmethyl)benz(cd)indol-2-amine, fumarate | 95 |
| N-(4-Pyridinylmethyl)benz(cd)indol-2-amine, sesqui-fumarate | 97 |
| N-(3-(3-Pyridinyloxy)propyl)benz(cd)-indol-2-amine, fumarate | 94 |
| 6-Bromo-N(4-(3-pyridinyl)butyl)benz-(cd)indol-2-amine sesqui-fumarate | 92 |
| N-(3-(3-Pyridinyl)propyl)benz(cd)-indol-2-amine, fumarate | 97 |
| N-(4-(2-Pyridinyl)butyl)benz(cd)-indol-2-amine, sesqui-fumarate | 89 |
| N-(2-(4-Pyridinyl)ethyl)benz(cd)-indol-2-amine, sesqui-fumarate | 88 |
| N-Benz(cd)indol-2-yl-N-(3-(3-pyridinyl)propyl)acetamide | 95 |
| N-(2-(2-Pyridinyl)ethyl)benz(cd)-indol-2-amine, fumarate | 94 |
| N-(5-(3-Pyridinyl)-3-pentenyl)benz(cd)-indol-2-amine, sesqui-fumarate | 99 |
| N-(2-Cyanoethyl)-N-(2-pyridinylmethyl)-benz(cd)indol-2-amine, dihydrochloride | 97 |
| N-Methyl-N-(2-(2-Pyridinyl)ethyl)benz-(cd)indol-2-amine, fumarate | 89 |
| N-(3-(4-Pyridinyl)butyl)benz(cd)indol-2-amine | 95 |
| N-(3-(3-Pyridinyl)butyl)benz(cd)indol-2-amine | 96 |
| N-(2-Methyl-3-(3-pyridinyl)propyl)benz-(cd)indol-2-amine, fumarate | 99 |
| 6,8,-Dichloro-N-(4-(3-pyridinyl)butyl) benz(cd)indol-2-amine | 93 |
| 6-Bromo-N-(4-(3-pyridinyl)butyl)benz-(cd)indol-2-amine, dihydrochloride | 89 |
| N-(2-(1-Methyl-1H-pyrrol-2-yl)ethyl)-benz(cd)indol-2-amine, fumarate | 90 |
| N-(2-Phenyl-2H-1,2,3-triazol-2-yl)-methyl)benz(cd)indol-2-amine, fumarate | 73 |
| N-(2-Thienylmethyl)benz(cd)indol-2-amine, fumarate | 93 |
| N-(2-Furanylmethyl) benz(cd)indol-2-amine, fumarate | 93 |
| N-Benz(cd)indol-2-yl-N-(2-1H-1,2,4-triazol-1-yl)propyl)acetamide | 62 |
| N-Benz(cd)indol-2-yl-N-(3-(1H-1,2,4-triazol-1-yl)propyl)benzamide | 77 |
| N-(4-(1H-imidazol-1-yl)butyl)benz(cd)indol-2-amine monobutanedioic acid salt | 93 |
| N-(4-(1H-imidazol-1-yl)butyl)benz(cd)indol-2-amine sesquibutanedioic acid salt | 98 |

The novel compounds of the present invention have been found to be highly useful for inhibiting thromboxane synthetase in mammals when administered in amounts ranging from about 1.0 mg to about 20.0 mg/kg of body weight per day. A preferred dosage regimen for optimum results would be from about 1.0 mg to about 10 mg/kg of body weight per day. Such dosage units are employed that a total of from about 70 to about 700 mg of active compound for a subject of about 70 kg of body weight are administered in a 24 hour period. This dosage regiment may be adjusted to provide the optimum therapeutic response. For example, several divided doses may be administered daily or the dose may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Hypotensive Activity in Spontaneously Hypertensive Rats

The novel compounds of the present invention are active hypotensive agents and were tested for hypotensive activity by the method of P. S. Chan and D. Poorvin, Clinical and Experimental Hypertension, 1 (6), 817-830 (1979). Male, 16 week old, spontaneously hypertensive rats of the Okamoto strain, from Taconic Farms, Germantown, N.Y., having an average mean arterial blood pressure of 160±1.5 mm of mercury, were used in the test. One to 4 rats were used per test compound. A rat was dosed by gavage with a test compound, suspended in 2% pre-boiled starch at a concentration of 50 mg/ml, at a doses of 10 mg/kg of body weight or less, with 0.9% sodium chloride loading at a dose of 25 ml/kg of body weight. A second identical dose of the test compound, without sodium chloride loading was given 24 hours later. At 28 hours after initial dose the mean arterial blood pressure (MABP) was measured. The procedure was repeated in a second and third rat when necessary.

The results of this test on representative compounds of the present invention appear below in Table II.

TABLE II

Hypotensive Activity

| Compound | Avg. MABP in mm Hg (No. of Rats) |
|---|---|
| N-(3-(1H-imidazol-1-yl)propyl)benz(cd)indol-2-amine, dihydrochloride | 87(2) |
| 6-Bromo-N-(3-(1H-imidazol-1-yl)propyl)-benz(cd)indol-2-amine, dihyrdrochloride | 117(2) |
| N-(3-(1H-imidzaol-1-yl)butyl)benz(cd)-indol-2-amine, dihydrochloride | 104(2) |
| N-(3-(4-methyl-1H-imidazol-1-yl)propyl)-benz(cd)indol-2-amine, dihydrochloride | 106(2) |
| N-(3-(1H-imidazol-1-yl)-2-methylpropyl)-benz(cd)indol-2-amine, dihydrochloride | 113(2) |
| N-(5-(1H-imidazol-1-yl)pentyl)benz(cd)-indol-2-amine, fumarate | 111(2) |
| (Z)-N-(4-(1H-imidazol-1-yl)2-butenyl)-benz(cd)indol-2-amine, dihydrochloride | 77(2) |
| N-(3-(1H-imidazol-1-yl)-2, 2-diphenyl-propyl)benz(cd)indol-2-amine | 127(3) |
| (Z)-N-(4-(1H-imidazol-1-yl)-2-butenyl)-benz(cd)indol-2-amine, fumarate | 102(1) |
| N-(4-(1H-imidazol-1-yl)butyl)benz(cd)-indol-2-amine, hydriodide | 74(2) |
| (Z)-N-(4-(1H-imidazol-1-yl)-2-butenyl)-benz(cd)indol-2-amine, hydriodide | 106(2) |
| N-(3-(1H-benzimidazol-1-yl)propyl)benz-(cd)indol-2-amine, fumarate | 123(3) |
| N-(3-(1H-benzimidazol-1-yl)propyl)benz-(cd)indol-2-amine | 124(3) |
| N-(4-(1H-imidazol-1-yl)butyl)benz(cd)-indol-2-amine, fumarate | 106(2) |
| N-(5-(1H-imidazol-1-yl)-3-methylpentyl)-benz(cd)indol-2-amine, dihydrocloride | 92(2) |
| N-(10-(1H-imidazol-1-yl)decyl)benz(cd)-indol-2-amine, fumarate | 124(3) |
| N-(10-(1H-imidazol-1-yl)decyl)benz(cd)-indol-2-amine, dihydrochloride | 124(3) |
| N-(2-(1H-imidazol-1-yl)ethyl)benz(cd)-indol-2-amine | 100(2) |
| N-(2-(2-(1H-imidazol-1-yl)ethoxy)ethyl) -benz(cd)indol-2-amine, fumarate | 108(2) |
| N-(8-(1H-imidazol-1-yl)octyl)benz(cd)-indol-2-amine, dihydrochloride | 111(2) |

TABLE II-continued

Hypotensive Activity

| Compound | Avg. MABP in mm Hg (No. of Rats) |
|---|---|
| N-(2-(1H-imidazol-1-yl)ethyl)benz(cd)-indol-2-amine, fumarate | 97(2) |
| 6-Bromo-N-(3-(1H-imidazol-1-yl)butyl)-benz(cd)indol-2-amine | 120(2) |
| 6-Bromo-N-(4-(1H-imidazol-1-yl)butyl)-benz(cd)indol-2-amine | 120(2) |
| N-((4-(1H-imidazol-1-ylmethyl)phenyl)-methyl)benz(cd)indol-2-amine, fumarate | 121(3) |
| 6,8-Dichloro-N-(10-(1H-imidazol-1-yl)-decyl)benz(cd)indol-2-amine | 121(2) |
| 6,8-Dichloro-N-(3-(1H-imidazol-1-yl)-butyl)benz(cd)indol-2-amine | 102(2) |
| 6,8-Dichloro-N-(3-(1H-imidazol-1-yl)-propyl)benz(cd)indol-2-amine | 102(2) |
| 6,8-Dichloro-N-(4-(1H-imidazol-1-yl)-butyl)benz(cd)indol-2-amine | 115(2) |
| 6-Bromo-N-(5-(1H-imidazol-1-yl)pentyl)-benz(cd)indol-2-amine | 118(3) |
| 6,8-Dichloro-N-(5-(1H-imidazol-1-yl) pentyl)benz(cd)indol-2-amine | 119(2) |
| N-(4-(1H-imidazol-1-yl)pentyl)benz-(cd)indol-2-amine, fumarate | 97(2) |
| 6-Chloro-N-(4-(1H-imidazol-1-yl)-butyl)benz(cd)indol-2-amine, fumarate | 115(2) |
| 6-Chloro-N-(3(1H-imidazol-1-yl)-propyl)benz(cd)indol-2-amine | 124(4) |
| N-(12-(1H-imidazol-1-yl)dodecyl)benz-(cd)indol-2-amine | 133(2) |
| 6-Bromo-N-(12-(1H-imidazol-1-yl)-dodecyl)benz(cd)indol-2-amine | 128(3) |
| N-Benz(cd)indol-2-yl-N-(4-(1H-imidazol-1-yl)butyl)acetamide | 81(2) |
| N-(3-(1H-imidazol-1-yl)propyl)benz-(cd)indol-2-amine, bis-fumarate | 81(2) |
| N-(3-1H-imidazol-1-yl)propyl)-N-methylbenz(cd)indol-2-amine | 95(3) |
| N-Benz(cd)indol-2-yl-N-(3-(1H-imidazol-1-yl)propyl)acetamide | 102(2) |
| N-Benz(cd)indol-2-yl-N-(3-(1H-imidazol-1-yl)propyl)benzamide | 95(2) |
| N-Benz(cd)indol-2-yl-N-(3-(1H-imidazol-1-yl)propyl)benzenesulfonamide | 135(1) |
| N-Benz(cd)indol-2-yl-N-(3-(1H-imidazol-1-yl)propyl)N'-phenylurea | 145(2) |
| N-Benz(cd)indol-2-yl-N-(4-(1H-imidazol-1-yl)butyl)propanamide | 83(2) |
| N-Benz(cd)indol-2-yl-2-chloro-N-(4-(1H-imidazol-1-yl)butyl)benzamide | 80(2) |
| N-(7-(1H-imidazol-1-yl)heptyl)benz-(cd)indol-2-amine | 127(2) |
| N-(2-(4-(1H-imidazol-1-yl)butyl)benz-(cd)indol-6-yl)-4-methylbenzenesulfonamide monoacetate | 125(2) |
| N-(3-(1H-imidazol-1-yl)-2-hydroxy-propyl)benz(cd)indol-2-amine bis-fumarate | 132(2) |
| 6,8-Dichloro-N-(3-(1H-imidazol-1-yl)-butyl)benz(cd)indol-2-amine dihydrochloride | 134(3) |
| 6,8-Dichloro-N-(3-(1H-imidazol-1-yl)-2-methylpropyl)benz(cd)indol-2-amine sesqui-furamate | 116(2) |
| 6,8-Dichloro-N-(7-(1H-imidazol-1-yl)-heptyl)benz(cd)indol-2-amine dihydrochloride | 130(2) |
| N-((2-Ethyl-2-(1H-imidazol-1-yl)methyl) butyl benz(cd)indol-2-amine, sesquifumarate | 112(2) |
| 6-Bromo-N-(3-(1H-imidazol-1-yl)-2-methylpropyl)benz(cd)indol-2-amine, dihydrochloride | 107(2) |
| N-Benz(cd)indol-2-yl-N-(4-(1H-imidazol-1-yl)butyl)-2-methoxybenzamide | 76(2) |
| N-Benz(cd)indol-2-yl-N-(4-(1H-imidazol-1-yl)butyl)-3-triflurومethylbenzamide | 77(2) |

TABLE II-continued

| Hypotensive Activity | |
|---|---|
| Compound | Avg. MABP in mm Hg (No. of Rats) |
| 6-Fluoro-N-(3-(1H-imidazol-1-yl)-propyl)benz(cd)indol-2-amine | 94(2) |
| Benz(cd)indol-2-yl-N-(4-(1H-imidazol-1-yl)butyl)valeramide | 84(2) |
| N-Benz(cd)indol-2-yl-N-(4-(1H-imidazol-1-yl)butyl)heptanamide | 76(2) |
| N-Benz(cd)indol-2-yl-N-(4-(1H-imidazol-1-yl)butyl)hexanamide | 102(2) |
| N-(4-(1H-imidazol-1-yl)butyl)benz(cd)-indol-2-amine, dimethiodide | 110(2) |
| N-(4-(1H-imidazol-1-yl)butoxy)benz(cd)-indol-2-amine | 111(2) |
| N-(Benz(cd)indol-2-yl)N-(4-(1H-imidazol-1-yl)butyl)benzamide | 80(2) |
| N-(Benz(cd)indol-2-yl)-N-(4-(1H-imidazol-1-yl)butyl)-2-furancarboxamide | 96(2) |
| N-(Benz(cd)indol-2-yl)-4-fluoro-N-(4-(1H-imidazol-1-yl)butyl)benzamide | 85(2) |
| N-(Benz(cd)indol-2-yl)-N-(4-(1H-imidazol-1-yl)butyl)-4-methylbenzamide | 82(2) |
| N-(Benz(cd)indol-2-yl)-N-(4-(1H-imidazol-1-yl)butyl)-2-thiophenecarboxamide | 86(2) |
| N-(Benz(cd)indol-2-yl)-3,4-dichloro-N-(4-(1H-imidazol-1-yl)butyl)benzamide | 96(2) |
| N-(2-(3-Pyridinyl)ethyl)benz(cd)indol-2-amine sesqui-fumarate | 126(4) |
| N-(4-(3-Pyridinyl)butyl)benz(cd)indol-2-amine sesqui-fumarate | 95(2) |
| N-(2-(2-Pyridinyloxy)ethyl)benz(cd)-indol-2-amine fumarate | 140(2) |
| N-(4-Pyridinylmethyl)benz(cd)indol-2-amine sesqui-fumarate | 90(2) |
| N-(3-(3-Pyridinyloxy)propyl)benz(cd)-indol-2-amine fumarate | 116(2) |
| 6-Bromo-N-(4-(3-(pyridinyl)butyl))benz-(cd)indol-2-amine, sesqui-fumarate | 110(2) |
| N-(3-(3-Pyridinyl)propyl)benz(cd)-indol-2-amine fumarate | 93(2) |
| N-(4-(2-Pyridinyl)butyl)benz(cd)-indol-2-amine sesqui-fumarate | 106(2) |
| N-(2-(4-Pyridinyl)ethyl)benz(cd)-indol-2-amine sesqui-fumarate | 115(2) |
| N-Benz(cd)indol-2-yl-N-(3-(3-pyridinyl)-propyl)acetamide | 85(2) |
| N-(2-(2-Pyridinyl)ethyl)benz(cd)-indol-3-amine-fumarate | 137(2) |
| N-(5-(3-Pyridinyl)-4-pentenyl)benz(cd)-indol-2-amine sesqui-fumarate | 140(2) |
| N-(3-(3-Pyridinyl)butyl)benz(cd)-indol-2-amine | 110(2) |
| N-(2-Methyl-3-(3-pyridinyl)propyl)-benz(cd)indol-2-amine fumarate | 124(1) |
| 6,8-Dichloro-N-(4-(3-pyridinyl)butyl)-benz(cd)indol-2-amine | 102(2) |
| 6-Bromo-N-(4-(3-pyridinyl)butyl)benz-(cd)indol-2-amine dihydrochloride | 99(2) |
| N-(2-((2-Pyridinylmethyl)thio)ethyl)-benz(cd)indol-2-amine fumarate | 143(2) |
| N-(Benz(cd)indol-2-yl)-N-(4-(3-pyridyl)butyl)-3-trifluoromethyl-benzamide | 115(1) |
| N-(1-(4-Chlorophenyl)-2-(1H-1,2,4-triazol-1-yl)ethyl)benz(cd)indol-2-amine fumarate | 142(2) |
| N-(3-(1H-Pyrazol-1-yl)propyl)benz(cd)-indol-2-amine fumarate | 141(2) |
| N-Benz(cd)indol-2-yl-N-(3-(1H-1,2,4-triazol-1-yl)propyl)acetamide | 118(2) |
| N-(2-Thienylmethyl)benz(cd)indol-2-amine fumarate | 141(2) |
| N-(2-Furanylmethyl)benz(cd)indol-2-amine fumarate | 142(2) |
| N-(2-(1H-imidazol-1-yl)ethyl)benz-(cd)indol-2-amine | 101(2) |
| N-(3-(4-Methyl-2-thiazolyl)propyl)-benz(cd)indol-2-amine fumarate | 122(2) |

The compounds of this invention are also considered to be cardio-protective in that they are anti-arrhythmic agents as established in the following test.

Thevetin (Cardiac Glycoside)-Induced Arrhythmia in Guinea Pigs

Male guinea pigs, weighing 300–500 g each, from Summit View Farms, Belvidere, N.J., were anesthetized by intraperitoneal adminstration of urethan at 1500 mg/kg. The animals were then restrained in a supine position. Electrocardiogram leads were attached to the four limbs and Lead II of the electrocardiogram was monitored.

The neck region was exposed and the jugular vein was cannulated. The test compounds were dissolved in saline and administered intravenously at the indicated doses, via a cannula which was then flushed with saline. Five minutes after the test compound was administered, thevetin dissolved in saline was administered by infusion through a cannula at a dose of 0.1 mg/kg/minute in a volume of 0.1 ml. The time until the P wave of the electrocardiogram disappeared was determined.

Based on the data obtained from 126 guinea pigs treated with physiological saline, but no test compound, the time it took for thevetin infusion to cause P wave disappearance on the electrocardiogram or the appearance of irregular heart beat (ectopic heart beat, etc.) was 22.91±0.5 minutes (means±S.E.M.).

A compound that protects guinea pigs for 31 minutes before arrhythmia occurred is considered active.

Propanolol at an intravenous dose of 2 mg/kg protected the guinea pigs for 47.0±4.1 minutes before arrhythmia occurred and was active in this test.

4-(2-(1H-imidazol-1-yl)ethoxy)benzoic acid, monohydrochloride (Dazoxiben hydrochloride, Pfizer, Inc.) and 2-methyl-3-(4-(3-pyridinylmethyl)phenyl-2-propenoic acid, sodium salt (OKY-1581, Ono Pharm.), both literature-described thromboxane synthetase inhibitors, at intravenous doses as high as 20 mg/kg were inactive (22.2±1.9 and 24.3±2.2 minutes, respectively).

The results of this test on typical compounds of this invention appear in Table III.

TABLE III

| Compound | No. of Guinea | IV Dose (mg/kg) | Time (Minutes) Before Induced Arrhythmia |
|---|---|---|---|
| N-(3-(1H-imidazol-1-yl)propyl)benz(cd)indol-2-amine, dihydrochloride | 4 | 10 | 48.5 |
| N-(3-(1H-imidazol-1-yl)-2-methyl-propyl)-benz(cd)indol-2-amine, fumarate | 4 | 20 | 34.5 |
| N-(3-(H-imidazol-1-yl)-2,2-diphenyl-propyl)-benz(cd)indol-2-amine | 4 | 10 | 41 |
| N-(4-(1H-imidazol-1-yl)butyl)benz(cd)-indol-2-amine, fumarate | 6 | 10 | 31 |
| N-(10-(1H-imidazol-1-yl)decyl)benz(cd)-indol-2-amine, fumarate | 6 | 10 | 34.2 |
| 6-Bromo-N-(3-(1H-imidazol-1-yl)butyl)-benz(cd)-indol-2-amine | 3 | 30 | 34.7 |
| 6,8,-Dichloro-N-(3-(1H-imidazol-1-yl)- | 6 | 20 | 32 |

TABLE III-continued

| Compound | No. of Guinea | IV Dose (mg/kg) | Time (Minutes) Before Induced Arrhythmia |
|---|---|---|---|
| butyl)-benz(cd)indol-2-amine | | | |
| 6,8-Dichloro-N-(5-(1H-imidazol-1-yl)-pentyl)-benz(cd)indol-2-amine | 5 | 20 | 33.4 |
| 6-Chloro-N-4-(1H-imidazol-1-yl)butyl)-benz(cd)indol-2-amine, fumarate | 2 | 10 | 31.5 |
| 6-Bromo-N-(5-(1H-imidazol-1-yl) pentyl)-benz(cd)indol-2-amine | 2 | 20 | 37 |
| 2-((3-(1H-imidazol-1-yl)butyl)amino) -N,N-dimethylbenz(cd)indole-6-sulfonamide | 9 | 10 | 33.6 |
| N-(3-(1H-imidazol-1-yl)-1-phenyl-propyl)-benz-(cd)indol-2-amine, fumarate | 8 | 30 | 34 |
| (E)-N-(4-(1H-imidazol-1-yl)-2-buten-yl)-benz(cd)indol-2-amine, mono-hydriodide | 3 | 10 | 34.3 |
| 2-((3-(1H-imidazol-1-yl)propyl) amino)-N,N'-dimethylbenz(cd)indole-6-sulfonamide | 5 | 20 | 33.4 |
| 2-(Benz(cd)indol-2-ylamino)-N-(3-(1H)-imidazol-1-yl)propyl)acetamide | 2 | 25 | 33 |
| N-(2-(3-Pyridinyl)ethyl)benz(cd) indol-2-amine sesqui-fumarate | 2 | 20 | 37 |

It is known that drugs that have alphaadrenoceptor binding activity are capable of blocking alpha-adrenoceptors on the heart muscle and are thus implicated in the prevention of several injuries that are associated with myocardial infarction.

In Vitro Test for Alpha-Adrenoceptor Binding in Heart Membrane

Myocardial membrane protein was isolated from Sprague-Dawley rats by an art recognized method. Each test compound was then incubated at a concentration of 10 micro-moles, in the presence if a know amount of membrane (about 500 micro-grams) and a radioactive ligand, $3_H$-prazocin. Displacement of the ligand by the test compound was then calculated by assessing the amount of radioactivity associated with membrane using a liquid scintillation counter. Specific binding of 65% or more of the total radioactivity to the membrane in the presence of the test compound is the criterion for designating a particular compound as "in vitro active". The results of this test appear in the following Table.

In Vitro Results for Alpha-Adrenoceptor Binding in Heart Membrane

| Compound | Percent* Specific Binding |
|---|---|
| N-(3-(2-Methyl-1H-imidazol-1-yl)propyl)-benz(cd)indol-2-amine, monohydriodide | 66.7 |
| N-(4-(1H-imidazol-1-yl)butyl)benz(cd)-indol-2-amine, fumarate | 78.4 |
| N-(10-(1H-imidazol-1-yl)decyl)benz(cd)-indol-2-amine, fumarate | 64.8 |
| N-(10-(1H-imidazol-1-yl)decyl)benz(cd)-indol-2-amine, dihydrochloride | 87.1 |
| N-(4-(1H-imidazol-1-yl)pentyl)benz(cd)-indol-2-amine, fumarate | 65.3 |
| 6-Chloro-N-(4-(1H-imidazol-1-yl)butyl)-benz(cd)indol-2-amine, fumarate | 65.6 |
| N-(3-1H-imidazol-1-yl)propyl)benz(cd)-indol-2-amine, difumarate | 71.7 |
| N-(3-(1H-imidazol-1-yl)-2-methyl)propyl-benz(cd)indol-2-amine fumarate | 67.0 |
| 6-Bromo-N-(10-(1H-imidazol-yl)decyl)-benz(cd)indol-2-amine | 66.7 |
| N-(3-(3-Pyridinyloxy)propyl)benz(cd)-indol-2-amine fumarate | 85.1 |
| N-(3-(3-Pyridinyl)propyl)benz(cd)indol 2-amine-fumarate | 76.1 |
| 6-Bromo-N-(4-(3-pyridinyl)butyl)benz-(cd)indol-2-amine fumarate | 68.4 |

*Mean of three separate incubations containing test compound at 10 micro-moles and 2.5 nM of $3_H$-prazocin.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have a molecular weight of from about 200 to 1500. Although the amount of active compound dissolved in the above vehicle may vary from 0.10% to 10.0% by weight, it is preferred that the amount of the active compound employed by from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gama-picolinium chloride, benzalkonium chloride, phenethyl alcohol, p-chlorophenyl-glycerol ether, methyl and propyl parabens, and thiomerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg/ml of the finished compositions. The novel compounds of the present invention are equally adapted to intravenous adminstration when diluted with water or diluents employed in intravenous therapy such isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, exlixirs, suspensions, syrups, wafers, and the like. Such compositions and preparations should contain at least 0.1% of active compound.

The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to modify otherwise the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

N-(3-(1H-imidazol-1-yl)propyl)benz(cd) indol-2 -amine, dihydrochloride

A mixture of 6.2 g of benz(cd)indole-2-thiol and 4.4 g of 3-(1H-imidazol-1-yl)propanamine in 250 ml of ethanol was stirred and heated. An 8.0 g portion of mercuric oxide was added, the mixture was stirred at reflux for 20 hours, then filtered and the insolubles washed with 100 ml of hot ethanol. The combined filtrate and wash was taken to dryness in vacuo. The residual oil was dissolved in a mixture of 100 ml of water and 15 ml of concentrated hydrochloric acid, treated with activated charcoal and then filtered. The filtrate was taken to dryness in vacuo. The residual oil was mixed with 150 ml of ethanol and taken to dryness in vacuo. This residue was dissolved in 100 ml of boiling ethanol, then filtered and the filtrate cooled at −10° C. This filtrate was then reheated to boiling, 300 ml of acetone were added, the mixture treated with activated charcoal and then filtered. The filtrate was cooled at −10° C. and the resulting preciptate collected, washed with acetone and dried in vacuo at 60° C., giving 3.4 g of the desired product, mp 262° C.–265° C.(dec.).

EXAMPLE 2

6-Bromo-N-(3-(1H-imidazol-1-yl)propyl)benz(cd)indol-2-amine, dihydrochloride

A mixture of 4.0 g of 6-bromo-2-benz(cd)indole-2-thiol and 2.0 g of 3-(1H-imidazol-1-yl)propanamine in 125 ml of 2-methoxyethanol was stirred and heated. An 3.8 g portion of mercuric oxide was added and the mixture was stirred at reflux for 7 hours, then clarified while hot. The filtrate was cooled at −10° C., acidified then 5 ml of concentrated hydrochloric acid and then taken to dryness in vacuo. The residue was dissolved in 150 ml of boiling ethanol, filtered, cooled to −10° C. and 150 ml of acetone added. This mixtures was allowed to stand at 10° C., then the precipitate was collected, washed with acetone and dried in vacuo at 60° C., giving 1.5 g of the desired product, mp 281° C.–283° C.(dec.).

EXAMPLE 3

N-(3-(1H-imidazol-1-yl)butyl)benz(cd) indol-2 -amine, dihydrochloride

A mixture of 2.8 g of 3-(1H-imidazol-1-yl)butanamine, and 250 ml of ethanol was stirred at reflux for 16 hours, then 2 g of potassium carbonate and 10 ml of water were added and the mixture was taken to dryness in vacuo. The residue was partitioned between 250 ml of dichloromethane and 100 ml of water. The dichloromethane layer was separated, dried over magnesium sulfate, filtered and the filtrate taken to dryness in vacuo. The residue was mixed with 200 ml of 2-methoxyethanol and 5 ml of concentrated hydrochloric acid, then taken to dryness in vacuo. The residue was dissolved in 50 ml of hot ethanol, diluted with 200 ml of acetone, cooled to −10° C., diluted with 200 ml of ether and then filtered. The filtrate was diluted with 400 ml of ether and cooled at −10° C. The precipitate was collected, washed with ether and dried in vacuo at 60° C., giving 0.8 g of the desired product, mp 145° C.–150° C. (dec.).

EXAMPLE 4

N-(1-(4-Chlorophenyl)-2-(1H-imidazol-1-yl)ethyl)-ben(cd)indol-2-amine, fumarate

A mixture of 2 g of 1-(4-chlorophenyl)-2-(1H-imidazol-1-yl) ethanamine, 2.95 g of 2-(methylthio)-benz(cd)indole hydriodide and 200 ml of ethanol was reacted as described in Example 3. The resulting base was dissolved in 50 m of acetone, filtered and the filtrate added to a solution of 0.3 g of fumaric acid in 50 ml of acetone. The mixture was cooled to −10° C., the solid collected, washed with acetone and ether and dried at 60° C. in vacuo, giving 0.6 g of the desired product, mp 130° C.–135° C. (dec.).

EXAMPLE 5

N-(3-(4-Methyl-1H-imidazol-1-yl)propyl)benz(cd)indol-2-amine, dihydrochloride

A 1.4 g portion of 3-(4-methyl-1H-imidazol-1-yl)propanamine, 1.9 g of benz(cd)indole-2-thiol, 250 ml of ethanol and 2.5 g of mercuric oxide were reacted as described in Example 1, giving 0.3 g of the desired product, mp 250° C.–255° C. (dec).

EXAMPLE 6

N-(3-1H-imidazol-1-yl)-2-methylpropyl)benz(cd)indol-2-amine, dihydrochloride

A mixture of 7 g of 2-methyl-3-(1H-imidazol-1-yl)propanamine, 9.3 g of benz(cd)indole-2-thiol, 300 ml of ethanol and 13 g of mercuric oxide was reacted as described in Example 1, giving 1.2 g of the desired product, mp 250° C.–255° C. (dec).

EXAMPLE 7

N-(3-(1H-imidazol-1-yl)-1-phenylpropyl)benz(cd)indol-2-amine, fumarate

A mixture of 4 g of phenyl-3-(1H-imidazol-1-yl)propanamine, 3.7 g of benz(cd)indole-2-thiol, 250 ml of ethanol and 6 g of mercuric oxide was reacted as described in Example 1, giving the dihydrochloride salt of the desired product, which was then converted to the fumarate salt giving 0.7 g of the desired product, mp 125° C.–127° C.

EXAMPLE 8

N-(3-(1H-imidazol-1-yl)-2-methylpropyl)benz(cd)indol-2-amine, fumarate

A portion of the corresponding dihydrochloride salt, prepared in Example 6, was reacted as described in Example 4, giving 0.7 g of the fumarate salt, mp 150° C.–154° C.

EXAMPLE 9

N-(5-(1H-imidazol-1-yl)pentyl)benz(cd)indol-2-amine, fumarate

A mixture of 1.55 g of 5-(1H-imidazol-1-yl)pentanamine, 3.3 g of 2-(methylthio)benz(cd)indole hydriodide, and 200 ml of ethanol was reacted as described in Example 3, giving 4.6 g of the corresponding dihydrochloride salt, which was further reacted as described in Example 4, giving 1.6 of the desired product, mp 159° C.–161° C. (dec.).

EXAMPLE 10

(Z)

N-(4-(1H-imidazol-1-yl)-2-butenyl)benz(cd)indol-2-amine, dihydrochloride

A mixture of 2.5 g of (Z)-(1H-imidazol-1-yl)-2-butenamine, 5.9 of 2-(methylthio)benz(cd)indole hydriodide, and 500 ml of ethanol was reacted as described in Example 3, giving 0.7 g of the desired product, mp 215° C.–220° C. (dec.).

EXAMPLE 11

N-(3-(1H-imidazol-1-yl)-2,2-diphenyl)propyl)benz(cd)indol-2-amine

A mixture of 3.3 g of 2-(methylthio)benz(cd)indole hydriodide, 1.8 g of 1H-imidazole-1-(2,2-diphenyl)-propanamine, 200 ml of ethanol and 0.9 g of sodium acetate was stirred at reflux for 18 hours, then diluted with 150 ml of water containing 1 g of sodium bicarbonate. This mixture was concentrated to turbidity and cooled at −10° C. The mixture was divided into two portions and each was extracted with two 200 ml portions of dichloromethane. All four extracts were combined, washed with 250 ml of water, dried over magnesium sulfate and filtered. The filtrate was evaporated at 40° C. The residual oil was extracted with two 100 ml portions of boiling hexane. The hexane was decanted, the residual solid washed with hexane, air dried and recrystallized from 200 ml of ethyl acetate, giving 1.3 g of the desired product, mp 229° C.–230° C.

EXAMPLE 12

(Z)-N-(4-(1H-imidazol-1-yl)-2-butenyl)benz(cd)indol-2-amine and the corresponding fumarate salt A mixture of 3.3 g of 2-(methylthio)benz(cd)indole hydriodide, 2.2 g of (Z)-4-(1H-imidazol-1-yl)- 2-butenamine, 200 ml of ethanol and 0.9 g of sodium acetate was reacted as described in Example 11, giving the desired base which was then converted to the corresponding fumarate salt as described in Example 4, giving 1.8 g of the desired product, mp 85° C.–90° C. (dec.).

EXAMPLE 13

N-(3-(2Phenyl-1H-imidazol-1-yl)-propyl)benz(cd)indol-2-amine, monohydriodide

A mixture of 4.0 of 3-(2-phenyl-1H-imidazol-1-yl)propanamind, 6.5 g of 2-(methylthio)benz(cd)indole hydriodide, 1.8 g of sodium acetate and 250 ml of ethanol was reacted as described in Example b 11. The crude produce was recrystallized from a mixture to ethanol and ispropanol giving 3.8 g of the desired product, mp 153° C.–155° C.

EXAMPLE 14

N-(3-(2Methyl-1H-imidazol-1-yl)propyl)benz(cd)indol-2-amine, monohydriodide

A mixture of 2.1 g of 3-(2-methyl-1H-imidazol-1-yl)propanamine, 5.0 g of 2-(methylthio)benz(cd)indole hydriodide, 1.4 g of sodium acetate and 250 ml of ethanol was reacted as described in Example 13, giving 1.0 g of the desired product, mp 153° C.–155° C.

EXAMPLE 15

N-(4-(1H-imidazol-1-yl)butyl)benz(cd)indol-2-amine, monohydriodide

A solution of 10 g of 4-(1H-imidazol-1-yl)butanamine in 100 ml of ethanol was added to a stirred suspension of 65 g of 2-(methylthio)benz(cd)indole hydriodide in 400 of ethanol. The mixture was added to a stirred and heated under reflux for 3 hours and then cooled at −10° C. The resulting precipitate was collected, washed with 125 ml cold ethanol, 250 ml of acetone and dried, giving 70.9 g of the desired product, m.p. 214°–216° C.

EXAMPLE 16

(E)-N-(4-(1H-imidazol-1-yl)-2-butenyl)benz(cd)indol-2-amine, monohydriodide

A mixture of 5.0 g of (E)-4-(1H-imidazol-1-yl)-2-butenamine, 11.5 g of 2-(methylthio)benz(cd)indole hydriodide and 400 ml of ethanol was stirred and heated at reflux for 16 hours, then clarified while hot. The filtrate was concentrated to 250 ml, cooled to −10° C. and the resulting solid collected, washed with ethanol, ether and dried at 60° C. in vacuo, giving 9.3 g of the desired product, mp 152° C.–155° C. (dec.).

EXAMPLE 17

N-(3-(1H-Benzimidazol-1-yl)propyl)benz(cd)indol-2-amine and fumarate salt

A mixture of 2.6 g of 3-(1H-benzimidazol-1-yl) propanamine, 2.8 g of benz(cd)-indole-2-thiol, 3.8 g of mercuric oxide and 250 ml of ethanol was reacted as described in Example 1, giving 1.5 g of the desired base mp 191° C.–193° C., which was then converted to the fumarate salt as described in Example 4, giving 1.3 g of the desired product as fumarate salt, mp 155° C.–158° C.

EXAMPLE 18

N-(4-(1H-imidazol-1-yl)butyl)benz(cd)indol-2-amine, fumarate

A 2.2 g portion of 4-(1H-imidazol-1-yl)butanamine dihydrochloride and 2 ml of 10N sodium hydroxide in 200 ml of ethanol was stirred for 10 minutes and then treated with 3.2 g of 2-(methylthio)benz(cd)indole hydroxide. This mixture was heated at reflux for 16 hours, and then taken to dryness in vacuo. The residue was partitioned between 250 ml of dichloromethane and 100 ml of 1N sodium hydroxide. The dichloromethane layer was dried over magnesium sulfate, filtered and the filtrate evaporated giving the crude base derivative. This base was treated with 1.5 g of fumaric acid in 400 ml of acetone, giving 2.4 g of the desired product, mp 153° C.-155° C. (dec.).

EXAMPLE 19

N-(3-(1H-imidazol-l-yl)-3-methylpentlyl)benz(cd)indol-2-amine, dihydrochloride

A 2.9 portion of 5-(1H-imidazol-l-yl)-3-methylpentanamine in 350 ml of ethanol was treated with 5.5 g of 2-(methylthio)benz(cd)indole hydriodide and stirred at reflux for 18 hours. The mixture was concentrated to 175 ml, cooled to −10° C. and clarified. The filtrate was taken to dryness in vacuo and the residue partitioned between 250 ml of dichloromethane and 100 ml of 1N sodiumhydroxide. The dichloromethane layer was dried over magnesium sulfate, clarified and evaporated to dryness. The residue was dissolved in 400 ml of acetone, treated with 10 ml of 3.5N hydrochloric acid in ethanol, then concentrated to 200 ml on a steam bath and diluted to turbidity with ether. The mixture was cooled to −10° C. and the solid collected, washed with acetone and dried in vacuo at 60° C., giving 1.5 g of the desired product, mp 113° C.-116° C. (dec.).

EXAMPLE 20

N-(10-(1H-imidazol-l-yl)benz(cd)indol-2-amine, fumarate and dihydrochloride

A mixture of 6.6 g of 10-(1H-imidazol-l-yl)decanamine, 500 ml of ethanol and 9.8 g of 2-(methylthio)-benz(cd)indole hydriodide was reacted as described in Example 19, giving 9.7 g of the base form of the desired compound as brown oil. A portion of this base was converted to the desired fumarate salt by the procedure described in Example 4, giving 1.1 g, mp 135° C.-136° C.

A portion of the base derivative was converted to the dihydrochloride salt by treatment with hydrochloric acid in ethanol, giving 3.5 mp 103° C.-105° C.

EXAMPLE 21

N-(2-(1H-imidazol-l-yl)ethyl)benz(cd)indol-2-amine, base and fumarate salt

A mixture of 1.25 g of 2-(1H-imidazol-l-yl)ethanamine, 300 ml of ethanol, and 2.5 g of 2-(methylthio)-benz(cd)indole hydriodide was reacted as described in Example 19, giving 1.4 g of the base derivative, mp 172° C.-173° C.

A portion of this base was then converted the fumarate salt as described in Example 4, giving 1.0 g, mp 210° C.-212° C.

EXAMPLE 22

N-(2-(2-)1H-imidazol-l-yl)ethoxy)ethyl)benz(cd)indol-2-amine, fumarate

A mixture of 1.7 g of 2-(2-(1H-imidazol-l-yl)ethoxyethanamine), 600 ml of ethanol, and 3.2 g of 2-(methylthio)benz(cd)indole hydriodide was reacted as described in Example 19, giving the base derivative which was then converted to the fumarate salt by the procedure of Example 4, giving 2.1 g, mp 153° C.-154° C. (dec.).

EXAMPLE 23

N-(8-(1H-imidazol-l-yl)octyl)benz(cd)indol-2-amine, dihydrochloride

A mixture of 2.1 of 8-(1H-imidazol-l-yl)octanamine, 400 ml of ethanol, and 3.2 g of 2-(methylthio)benz(cd)indole hydriodide was reacted as described in Example 19, giving the base derivative which was then treated with hydrochloric acid giving 1.3 g of the desired hydrochloride salt, mp 222° C.-224° C.

EXAMPLE 24

N-(Benz(cd)indole-2-ylamino)-N-(3-(1H-imidazol-l-yl)propyl

A mixture of 3.7 g of N-(3-(1H-imidazol-l-yl)propyl)-glycinamide, 425 ml of ethanol, and 5.0 g of 2-(methylthio)benz(cd)indole hydriodide was reacted as described in Example 19, giving 2.2 of the desired product, mp 145° C.-146° C.

EXAMPLE 25

N-(4-(1H-imidazol-l-ylmethyl)phenyl)methyl)benz(cd)indol-2-amine, fumarate

A mixture of 2.8 g of 4-(1H-imidazol-l-yl) methylbenzylamine, 250 ml of ethanol and 4.7 g of 2-(methylthio)-benz(cd)indole hydriodide was reacted as described in Example 19 giving the base derivative which was then reacted as described in Example 4, giving 6.6 g of the fumarate salt, mp 200° C.-200° C.

EXAMPLE 26

N-(4-(1H-imidazol-l-yl)pentyl)benz(cd)indol-2-amine, fumarate

A mixture of 2.8 g of 4-(1H-imidazol-l-yl)pentanamine, 3.3 g of benz(cd)indole-2-thiol, 7.0 g of mercuric acetate and 500 ml of ethanol was reacted as described in Example 1, giving the base derivative which was converted to the fumarate slat as described in Example 4, giving 5.6 g, mp 173° C.-175° C.

EXAMPLE 27

6-Bromo-N-(3-(1H-imidazol-l-yl)butyl)benz(cd)indol-2-amine

A mixture of 5.2 g of 6-bromo-benz(cd)indole2-thiol, 2.8 g of 3-(1H-imidazol-l-yl)butanamine, 6.6 g of mercuric acetate and 100 ml of dry p-dioxane was reacted as described in Example 1, giving 3.0 g of the desired product, mp 240° C.-241° C.

EXAMPLE 28

2-((3-(1H-imidazol-l-yl)butyl)amino)N,N-dimethyl-benz(cd)indol-6-sulfonamide

A mixture of 7.3 g of 1,2-dihydro-N,N-dimethyl-2-thioxobenz(cd)indole-6-sulfonamide, 4.2 g of 3-(1H-imidazol-l-yl)butanamine, 150 ml of ethanol and 9.6 g of mercuric acetate was reacted as described in Example 1, giving 5.5 g of the desired product, mp 221° C.-222° C.

EXAMPLE 29

2-((3-(1H-imidazol-l-yl)propyl)amino)N,N-dimethyl-benz(cd)indol-6-sulfonamide

A mixture of 5.0 g of 1,2-dihydro-N,N-dimethyl-2-thioxobenz(cd)indole-6-sulfonamide, 2.3 g of 3-(1H-imidazol-l-yl)propanamine, 100 ml of ethanol and 5.4 g of mercuric acetate was reacted as described in Example 1, giving 2.7 g of the desired product, mp 199° C.-201° C.

EXAMPLE 30 6-Bromo-N-(10-(1H-imidazol-l-yl) decyl)benz(cd)indol-2-amine

A mixture of 2.8 g of 10-(1H-imidazol-l-yl)decanamine, dihydrochloride was treated with 2 ml of 10N sodium hydroxide in an ethanol-water mixture giving the base derivative. To this base was added 25 ml of ethanol, 2.33 g of 6-bromo-benz(cd)indole-2-thiol and 3.0 g of mercuric acetate. The procedure of Example 1 was then followed, giving 2.8 g of the desired product, mp 115° C.-116° C.

EXAMPLE 31

6-Bromo-N-(4-(1H-imidazol-l-yl)butyl)benz(cd)indol-2-amine

A mixture of 4.2 g of 4-(1H-imidazol-l-yl)butanamine dihydrochloride in 75 ml of ethanol was treated with 2.2 g of potassium hydroxide and stirred for 18 hours. A 5.2 g portion of 6-bromo-benz(cd)indole-2-thiol and 6.4 g of mercuric acetate were added and the reaction proceeded as described in Example 1, giving 3.7 g of the desired product, mp 145° C.-147° C.

EXAMPLE 32

6,8-Dichloro-N-(10-(1H-imidazol-l-yl)decyl)benz(cd)indol-2-amine

A 2.8 g portion of 10-(1H-imidazol-l-yl)decanamine, dihydrochloride in an ethanol-water mixture was treated with 2.0 ml of 10N sodium hydroxide, stirred and evaporated to dryness. To the residue was added 35 ml of dry dimethylformamide, 3 g of mercuric acetate and 2.2 g of 6, 8,-dichloro-benz(cd)indole-2-thiol. The reaction proceeded as described in Example 1, giving 2.3 g of the desired product, mp 129° C.-131° C.

EXAMPLE 33

6,8-Dichloro-N-(3-(1H-imidazol-l-yl)butyl)benz(cd)indol-2-amine

A mixture of 7.0 g of 6,8,-dichloro-benz(cd)indole-2-thiol, 100 ml of ethanol, 9.5 g of mercuric acetate and 4.2 g of 4-(1H-imidazol-l-yl)-2-butanamine was reacted as described in Example 1, giving 1.7 g of the desired product, mp 244° C.-246° C.

EXAMPLE 34

6,8-Dichloro-N-(3-(1H-imidazol-l-yl)propyl)benz(cd)indol-2-amine

A mixture of 5.0 g of 6,8-dichloro-benz(cd) indole-2-thiol, 35 ml of dimethylformamide, 2.6 g of 3-(1H-imidazol-yl)propanamine and 6.3 g of mercuric acetate was reacted as described in Example 1, giving 2.95 g of the desired product, mp 182° C.-183° C.

EXAMPLE 35

6,8-Dichloro-N-(4-(1H-imidazol-l-yl)butyl)benz(cd)indol-2-amine

A 4.2 g portion of 4-(1H-imidazol-l-yl)butanamine, dihydrochloride was suspended in 75 ml of ethanol, treated with 2.24 g of potassium hydroxide, stirred for 6 hours and evaporated. A 35 ml portion of dimethylformamide, 5.0 g of 6,8-dichloro-benz(cd)indole-2-thiol, and 6.3 g of mercuric acetate were added and the reaction proceeded as described in Example 1, giving 2.5 g of the desired product, mp 187° C.-188° C.

EXAMPLE 36

6-Bromo-N-(5-(1H-imidazol-l-yl)pentyl)benz(cd)indol-2-amine

A mixture of 5.3 g of 6-bromo-benz(cd)indole-2-thiol, 3.1 g of 5-(1H-imidazol-l-yl) pentanamine, 100 ml of ethanol and 6.3 g of mercuric acetate was reacted as described in Example 1, giving 1.5 g of the desired product, mp 138° C.-140° C.

EXAMPLE 37

6,8-Dichloro-N-(5-(1H-imidazol-l-yl)pentyl)benz(cd)indol-2-amine

A mixture of 5.0 g of 6,8-dichloro-benz(cd)indole-2-thiol, 3.1 g of 5-(1H-imidazol-l-yl)pentanamine, 100 ml of dry dimethylformamide and 6.3 g of mercuric acetate was reacted as described in Example 1, giving 1.8 g of the desired product, mp 191° C.-192.5° C.

EXAMPLE 38

N-(12-(1H-imidazol-l-yl)dodecyl)benz(cd)indol-2-amine

A mixture of 2.5 g of 12-(1H-imidazol-l-yl)dodecanamine, 1.9 g of benz(cd)indole-2-thiol, 3.4 g of mercuric acetate and 400 ml of ethanol was reacted as described in Example 1. The crude product was purified by dissolved it in chloroform and chromatographing it on a silica gel column, eluting with 10% methanol in chloroform giving 490 mg of the desired product, mp 95° C.-97° C.

EXAMPLE 39

6-Bromo-N-(12-(1H-imidazol-l-yl)dodecyl)benz(cd)indol-2-amine

The procedure of Example 38 was repeated using 2.65 g of 6-bromo-benz(cd)indole-2-thiol instead of 1.9 g of benz(cd)indole-2-thiol, giving 720 mg of the desired product, mp 111° C.-116° C.

EXAMPLE 40

6-Chloro-N-(5-(1H-imidazol-l-yl)pentyl)benz(cd)indol-2-amine

A mixture of 4.4 g of 6-chloro-benz(cd)indole-2-thiol, 3.06 g of 5-(1H-imidazol-l-yl)pentanamine, 6.3 g of mercuric acetate and 150 ml of ethanol was reacted as described in Example 1, giving 5.2 g of the desired product, mp 132° C.-134° C.

EXAMPLE 41

6-Chloro-N-(4-(1H-imidazol-l-yl)butyl)benz(cd)indol-2-amine, fumarate

A mixture of 4.4 g of 6-chloro-benz(cd)indole-2-thiol, 2.8 g of 4-(1H-imidazol-l-yl)butanamine, 6.3 g of mercuric acetate and 150 ml of ethanol was reacted as described in Example 1, giving the free base form. This free base was converted to the fumarate salt by the procedure of Example 4, giving 4.8 g mp 190° C.-192° C.

EXAMPLE 42

6-Chloro-N-(3-(1H-imidazol-l-yl)propyl)benz(cd)indol-2-amine

A mixture of 1.0 g of 6-chloro-benz(cd)indole-2-thiol, 540 mg of 3-(1H-imidazol-l-yl) propanamine, 1.26 g of mercuric acetate and 100 ml of ethanol was reacted as described in Example 1, giving 1.0 g of the desired compound, mp 177° C.-178° C.

EXAMPLE 43

N-(3-(1H-imidazol-1-yl)propyl)benz(cd)indol-2-amine, difumarate

The free base, N-(3-(1H-imidazol-1-yl)propyl)benz(cd)indole-2-amine (prepared as described in Example 1) was dissolved in 20 parts (by weight) of acetone and this solution added dropwise to a vigorously stirred, refluxing solution of 2.2 equivalents of fumaric acid in 150 parts of acetone. After cooling to room temperature, the bright yellow precipitate was collected, washed with acetone and dried in vacuo at 60° C., giving the desired fumarate salt, mp 165° C.–166° C. (dec.).

EXAMPLE 44

Z-N-(4-(1H-imidazol-1-yl)-2-butenyl)benz(cd)indol-2-amine difumarate

The free base of the product of Example 10 was dissolved in acetone and added to a boiling solution of two equivalents of fumaric acid in acid. After cooling to room temperature, the bright yellow precipitate of the desired product was collected and dried. It melted at 111° C.–113° C.

EXAMPLE 45

N-Benz(cd)indol-2-yl-N-(4-(1H-imidazol-1-yl)butyl-)acetamide

A solution of five grams of N-(4-1H-imidazol-1-yl)butyl)benz(cd)indol-2-amine (free base of compound of Example 18)was dissolved in 50 ml of dichloromethane. Ten ml of acetic anhydride were added, and the solution then refluxed (steam bath) for two hours. The volatiles were removed in vacuo, and the residue partitioned between 100 ml of dichloromethane and 50 ml of saturated $NaHCO_3$ solution. The dichloromethane layer was separated, dried over sodium sulfate and then concentrated to dryness in vacuo. Trituration of the residue with 50 ml of acetone and filtration gave a precipitate of the desired compound; weight 2.5 grams; mp 127° C.–130° C.

EXAMPLE 46

N-(3-(1H-imidazol-1-yl)propyl-N-(phenyl)methyl)-benz(cd)indol-2-amine

The reaction of 4-(1H-imidazol-1-yl)butaneamine and benzaldehyde in ethanol, followed by reduction with sodium borohydride gave N-(phenylmethyl)-3-(1H-imidazol-1-yl)propanamine as a colorless viscous oil boiling at 150° C. (0.1 mm pressure).

2.1 grams of N-(phenylmethyl)-3-(1H-imidazol-1-yl)propanamine and 3.3 grams of 2-methylthiobenz(cd)indole hydriodide were added to 100 ml of ethanol and the mixture stirred and heated under reflux from 20 hours. It was taken to dryness in vacuo after the addition of 2 ml of 5N NaOH solution. The residue was triturated with 25 ml of chloroform, and the mixture filtered. The chloroform filtate was placed on 3 cm diameter 35 cm high silica gel calcium and chromatographed using 1:9 methanol:chloroform to develop the column. From the cuts containing the desired product, a viscous orange-yellow oil was obtained which crystallized upon trituation with cold acetone. The crystals were collected and dried in vacuo at room temperature; the yield of desired product was 1.2 grams, melting at 142° C.–143° C.

EXAMPLE 47

N-(3-(1H-imidazol-1-yl)-N-methylbenz(cd)indol-2-amine 12.3 ml of acetic anhydride was cooled below 0° C. and treated dropwise with 6.1 ml of 98% formic acid, keeping the reaction temperature below 0° C. by external cooling. The mixture was then slowly warmed, and kept at 50° C.–60° C. for two hours. 10 ml of tetrahydrofuran was added, and the solution of acetic formic anhydric cooled to −20° C. A solution of 6.2 g of 3-(1H-imidazol-1-yl)propanamine in 20 ml of tetrahydrofuran was then added dropwise, keeping the temperature below −10° C. The reaction mixture was allowed to come to room temperature, 10 ml of water was added, and the mixture taken to dryness in vacuo. Distillation of the viscous residue at 195° C.–200° C. gave 6.2 g of N-(3-(1H-imidazol-1-yl)propyl)formamide. This was reduced to N-methyl-3-(1H-imidazol-1-yl)propylamine by the use of borane dimethylsulfide in refluxing tetrahydrofuran.

The reaction of 1.0 g of N-methyl-3-(1H-imidazol-1-yl)propanamine and 2.3 g of 2-methyltiobenz(cd)indole hydriodide in 100 ml of refluxing ethanol for 14 hours, followed by 1.4 ml of 5N NaOH solution and concentration to dryness in vacuo gave a crude product which was purified by the procedure of Example 46. The yield of desired product was 0.97 g melting at 149° C.–150° C.

EXAMPLE 48

N-Benz(cd)indol-2-yl-N-(3-(1H-imidazol-1-yl)propyl-)acetamide

The desired compound was obtained by the procedure of Example 45, utilizing N-(3-(1H-imidazol-1-yl)propyl)benz(cd)indole-2-amine, (the free base of the compound of Example 1). The compound melted at 124.5° C.–128° C.

EXAMPLE 49

N-Benz(cd)indol-2-yl-N-(3-(1H-imidazol-1-yl)propyl)-benzamide

Five grams of N-(3-(1H-imidazol-1-yl)propyl)benz(cd)indole-2-amine (the free base of the compound of Example 1) and 100 mg of 4-dimethylaminopyridine were dissolved in 50 ml of pyridine. The solution was stirred as 2.8 grams of benzoyl chloride was slowly added. An exotherm was noted. The mixture was stirred at room temperature for 4 hours and then drowned onto 500 ml of ice. The precipitated solid was collected, washed with water, and dried. Recrystallization from chloroform-hexane gave 1.0 gram of desired compound, mp 148° C.–153° C., with decomposition.

EXAMPLE 50

N-Benz(cd)indol-2-yl-N-(3-(1H-imidazol-2-yl)propyl)-benzenesulfonamide

The procedure of Example 49 was utilized, 3.5 grams of benzenesulfonyl chloride being used in place of the benzoyl chloride. The crude product was recrystallized from dichloromethane-hexane, yielding 3.8 grams of desired product, mp 143° C.–145° C., with decomposition.

EXAMPLE 51

N-Benz(cd)indol-2-yl-N-(3-(1H-imidazol-1-yl)propyl)-N'-phenylurea

A solution of 2.7 g of N-(3-(1H-imidazol-1-yl)propyl)benz(cd)indol-2-amine (free base of the compound of Example 1) was dissolved in 50 ml of dichloromethane, and the solution then treated with 2.4 grams of phenylisocyanate. The mixture was stirred at room temperature overnight and then washed with 50 ml of saturated $NaCHO_3$ solution. The dichloromethane layer was dried over $MgSO_4$. Removal of the dichloromethane in vacuo left 3.7 grams of the desired compound, melting at 240° C.-250° C. with decomposition.

EXAMPLE 52

N-(2-Pyridinylmethyl)benz(cd)indol-2-amine fumarate

A mixture consisting of 4.9 grams of 2-methylthiobenz(cd)indole hydriodide, 1.7 grams of 2-pyridinylmethylamine, and 100 ml of ethanol was stirred and heated under reflux for 16 hours. After concentration to dryness in vacuo, the residue was partitioned between 250 ml of dichloromethane and 100 ml of 1N NaOH solution. The dichloromethane layer was dried over $MgSO_4$, and the dichloromethane removed in vacuo. The residual yellow-brown oil was dissolved in 100 ml of acetone and added to a stirred boiling solution of 3.5 grams of fumaric acid in 800 ml of acetone. A precipitate formed immediately. After cooling to room temperature, the precipitate was collected, washed with acetone and dried. The yield of desired product was 3.4 grams; mp 210° C.-213° C. with decomposition.

EXAMPLE 53

N-(4-Pyridinylmethyl)benz(cd)indol-2-amine sesqui-fumarate

The subject compound was prepared by the procedure of Example 52, 4-pyridinylmethylamine replacing the 2-pyridinylmethylamine. The yield was 3.5 grams and the compound melted at 180° C.-182° C. with decomposition.

EXAMPLE 54

N-(2-Furanylmethyl)benz(cd)indol-2-amine fumarate

The subject compound was prepared by the procedure of Example 52, 2-furanylmethylamine replacing the 2-pyridinylmethylamine. The yield of product was 4.4 grams, and the mp was 223° C.-225° C. with decomposition.

EXAMPLE 55

N-(3-Pyridinylmethyl)benz(cd)indol-2-amine fumarate

A mixture consisting of 3.7 grams of benz(cd)indole-2-thiol, 2.3 grams of 3-pyridinylmethylamine, and 300 ml of ethanol was stirred as 6.6 grams of mercuric acetate was added. The mixture was then stirred and heated under reflux for 16 hours, the slurry changing slowly from a yellow-brown color to a deep black. The hot mixture was filtered through diatomaceous earth; the black precipitate was washed with 100 ml of ethanol. After addition of 5 ml of 10N NaOH solution, the reaction mixture was taken to dryness in vacuo. The residue was partitioned between 250 ml dichloromethane and 100 ml of water. The dichloromethane layer was dried over $MgSO_4$, and the dichloromethane removed in vacuo. The residual orange-yellow oil was dissolved in 100 ml of acetone, and added to a stirred boiling solution of 5 grams of fumaric acid in 1200 ml of acetone. A heavy yellow precipitate formed at once. After cooling to room temperature, the precipitate was collected, washed with acetone and dried. The yield of subject compound was 5.9 g and the melting point was 192° C.-194° C. with decomposition.

EXAMPLE 56

N-(2-Thienylmethyl)benz(cd)indol-2-amine fumarate

The subject compound was prepared by the method of Example 55, 2.4 grams of 2-thienylmethylamine replacing the 3-pyridinylmethylamine. The yield was 2.9 grams and the mp was 208° C.-209° C. with decomposition.

EXAMPLE 57

N-(3-(3-Pyridinyl)propyl)benz(cd)indol-2-amine fumarate 3-(3-Pyridinyl)propylamine was prepared by the method described in *Helv. Chim. Acta.* 65 1868-1883 (1982).

The subject compound was prepared on a 0.05 mole scale by the procedure of Example 55, an equivalent of 3(3-pyridinyl)propylamine replacing the 3-pyridinylmethylamine. The yield was 16.1 grams and the mp was 192° C.-193° C. with decomposition.

EXAMPLE 58

N-(3-(3-Pyridinylyloxy)propyl)benz(cd)indol-2-amine-fumarate 3-(3-Pyridinyloxy)propylamine was prepared as follows: the reaction of N-(3-bromopropyl)phthalimide and the sodium salt of 3-pyridinol in hot dimethylformamide solution gave N-(3-(3-pyridinyloxy)propyl)phthalimide, which on treatment with hydrazine in boiling ethanol, gave the desired amine.

A mixture consisting of 2.3 grams of 3-(3-pyridinyloxy)propylamine, 2.8 grams of benz(cd)indo-2-thiol, and 250 ml of ethanol was stirred and 5.0 grams of mercuric acetate then added. The subsequent reaction conditions and workup procedure were those of Example 55. The yield of desired product was 4.6 grams and the mp was 174° C.-175° C. with decomposition.

EXAMPLE 59

N-(4-(2-Pyridinyl)butyl)benz(cd)indol-2-amine sesqui-fumarate 4-(2-Pyridinyl)butylamine was prepared by the method described in *Helv. Chim. Acta* 65 1868-1883 (1982).

The subject compound was prepared on a 0.02 molar scale by the procedure of Example 55, an equivalent of 4-(2-pyridinyl)butylamine replacing the 3-pyridinylmethylamine. The yield of the desired compound was 2.6 grams, and the mp was 130° C.-132° C. with decomposition.

EXAMPLE 60

6-Bromo-N-(4-(3-pyridinyl)butyl)benz(cd)indol-2-amine sesqui-fumarate 4-(3-Pyridinyl)butylamine was prepared by the procedure described in *Helv. Chim. Acta.* 65 1868-1883 (1982). 6-Bromobenz(cd)indol-2-thiol was prepared by the action of $P_2S_5$ upon 6-bromobenz(cd)indol-2-one in refluxing pyridine.

A mixture consisting of 2.6 grams of 6-bromobenz(c-d)indol-2-thiol, 1.5 grams of 4-(3-pyridinyl)butylamine, and 250 ml of ethanol was stirred as 3.5 grams of mercuric acetate was added. The mixture was stirred and heated under reflux for 16 hours, a deep balck slurry being formed. Twenty-five ml of 1N NaOH solution was added, and the insolubles filtered off. The cake was washed with ethanol. The filtrate was taken to dryness in vacuo, and the residue then partitioned between 200 ml of dichloromethane and 100 ml of water. The dichloromethane was dried over $MgSO_4$, and the dichloromethane removed in vacuo. The residual orange oil was dissolved in 100 ml of acetone, and the solution added to as stirred boiling solution of 3.0 grams of fumaric acid in 800 ml of acetone. A yellow precipitate formed at once. After cooling to room temperature, the precipitate was collected, washed with acetone, and dried. The yield of desired compound was 2.6 grams, mp 138° C.–140° C. with decomposition.

EXAMPLE 61

N-Benz(cd)indol-2-yl N-(4-(1H-imidazol-1-yl)butanamide

The title compound was prepared by the procedure of Example 45, an equivalent of n-butyric anhydride replacing the acetic anyhdride. The yield was 4.5 grams and the mp was 96° C.–98° C.

EXAMPLE 62

N-(2-(4-Pyridinyl)ethyl)benz(cd)indol-2-amine sesqui-fumarate

The title compound was prepared by the procedure of Example 52, an equivalent of 2-(4-pyridinyl)ethylamine replacing the 2-pyridinylmethylamine. The yield of the compound was 4.2 grams, and the mp was 173° C.–175° C. with decomposition.

EXAMPLE 63

N-(2-(1-Methyl-1H-pyrrol-2-yl)ethyl)benz(cd)indol-2-amine fumarate

The title compound was prepared by the procedure of example 52, an equivalent of 2-(1-methyl-1H-pyrrol-2-yl)ethylamine replacing the 2-pyridinylmethylamine. The yield was 4.6 grams, and the mp was 210° C.–212° C. with decomposition.

EXAMPLE 64

N-(7-(1H-imidazole-1-yl)heptyl)benz(cd)indol-2-amine

A mixture consisting of 5.0 grams of 2-methylthiobenz(cd)indol-2-amine hydriodide, 2.8 grams of 7-(1H-imidazol-1-yl)heptylamine, and 75 ml of ethanol as stirred and heated under reflux for 16 hours. After addition of 20 ml of 1N NaOH solution, the reaction mixture was taken to dryness in vacuo. The residue was partitioned between 150 ml of dichloromethane and 100 ml of water. A solid appeared at the interface. It was collected by filtration, added to the dichloromethane filtrate, and the mixture taken to dryness in vacuo. The residual orange oil was dissolved in 100 ml of acetone and added to a stirred boiling solution of 3.5 grams of fumaric acid in 800 ml of acetone. The resultant yellow precipitate was collected, washed with acetone, and dissolved in 200 ml of hot water. The solution was clarified by treatment with activated charcoal. The clear aqueous solution was cooled and made basic with 0.5 N NaOH solution. The resultant orange precipitate was collected, washed with water and dried in vacuo at room temperature. The yield of the title compound was 2.2 grams, and the mp was 48° C.–50°C.

EXAMPLE 65

N-Benz(cd)indol-2-yl-N-(3-(3-pyridinyl)propyl)acetamide

The subject compound was prepared by the procedure of Example 45, employing the free base of the compound of Example 57. After the purification by recrystallization from acetone, the desired compound melted at 113° C.–114° C.

EXAMPLE 66

N-(2-(2-pyridinyl)ethyl)benz(cd)indol-2-amine fumarate

The title compound was prepared by the procedure of Example 52, an equivalent of 2-(2-pyridinyl)ethylamine replacing the 2-pyridinylmethylamine. The yield of the compound was 3.5 grams, and the mp was 191° C.–193° C. with decomposition.

EXAMPLE 67

N-(5-(3-Pyridinyl)-3-pentyl)benz(cd)indol-2-amine sesqui-fumarate

The preparation of the intermediate 5-(3-pyridinyl)-3-pentenamine was accomplished as follows: reaction of N-(4-bromobutyl)phthalimide and triphenylphorphine, gave (4-(N-phthalimido)butyl)triphenylphosphonium bromide, which compound upon treatment with 3-pyridinecarboxaldehyde and sodium hydride in dimethylformamide solution (Witting Reaction) gave N-(5-(3-pyridinyl)-3-pentenyl)phthalimide. This latter compound upon treatment with hydrazine in refluxing ethanol gave the desired 5-(3-pyridinyl)-3-pentenamine.

A mixture consisting of 5.7 grams of 5-(3-pyridinyl)-3-pentenamine, 6.8 grams of 2-methylthiobenz(cd)indole hydriodide, and 150 ml of ethanol was stirred and heated under reflux for 20 hours. The crude free base was isolated by the procedure of Example 52, and purified by the chromatographic procedure of Example 46. Conversion of the isolated purified free base to the fumarate salt in boiling acetone solution gave 3.4 grams of the desired product, mp 198° C. with decomposition.

EXAMPLE 68

N-(2-Cyanoethyl)-N-(2-pyridinylmethyl)benz(cd)indol-2-amine dihydrochloride

The starting amine was prepared by the addition of 2-pyridylmethylamine to one equivalent of acrylonitrile.

A mixture consisting of 6.4 grams of N-(2-cyanoethyl)-2-pyridinylmethylamine, 7.4 grams of benz(cd)indol-2-thiol, and 200 ml of ethanol was stirred as 12.7 grams of mercuric acetate was added. The mixture was stirred and heated under reflux for 20 hours, a deep black slurry being present. The insolubles were separated by filtration and the filtrate taken by dryness in vacuo. The crude free base product was purified by the chromatographic procedure of Example 46. The purified free base was added to ethanolic hydrogen chloride, yielding 3.9 grams of the title compound, mp 224° C.–266° C.

EXAMPLE 69

N-(3-(1H-1,2,4-triazol-1-yl)propyl)benz(cd)indol-2-amine fumarate

A mixture consisting of 6.3 grams of 3-(1H-1,2,4-triazol-1-yl)propylamine, 9.3 grams of benz(cd)indol-2-thiol, and 13 grams of mercuric oxide and 300 ml of ethanol was stirred and heated under reflux for 16 hours. A black slurry developed quickly. The hot reaction mixture was filtered, and 10 ml of 10N NaOH was added to the filtrate, which was then taken to dryness in vacuo. The residue was partitioned between 200 ml of dichloromethane and 100 ml of water. The dichloromethane layer was dried over $MgSO_4$, and the dichloromethane removed in vacuo, leaving 13.2 g of the free base. 4.4 g was dissolved in 70 ml of acetone and added to a stirred boiling solution of 2.0 grams of fumaric acid in 500 ml of acetone. The yellow precipitate of the title compound was collected, washed with acetone, and dried; yield, 4.7 grams; mp 195° C.-198° C. with decomposition.

EXAMPLE 70

N-Benz(cd)indol-2-yl N-(3-(1H-1,2,4-triazol-1-yl)propyl)acetamide

Three and three-tenths grams of the free base of Example 69 and 10 ml of acetic anhydride were added to 5 ml of pyridine, and the mixture then refluxed for 15 minutes. The volatiles were removed in vacuo and the residue partitioned between 100 ml of dichloromethane and 100 ml of saturated $NaHCO_3$ solution. The dichloromethane layer was dried over $MgSO_4$. The dichloromethane solution was heated to boiling and hexane added until turbidity resulted (about 300 ml). The mixture was then cooled at −10° C. The precipitate of the title compound was collected, washed with hexane, and dried; yield, 1.9 grams; mp 128° C.-129° C.

EXAMPLE 71

N-Benz(cd)indol-2-yl N-(3-(1H-1,2,4-triazol-1-yl)propyl)benzamide

The title compound was prepared by the procedure of Example 70, utilizing 2.6 grams of N-(3-(1H-1,2,4-triazol-1-yl)benz(cd)indol-2-amine Example 69, 1.8 grams of benzoyl chloride, and 5 ml of pyridine. After recrystallization from dichloromethanehexane, the yield was 0.6 grams, mp 140° C.-141° C.

EXAMPLE 72

N-((2-Phenyl-2H-1,2,3-triazol-2-yl)methyl)benz(cd)indol-2-amine fumarate

The title compound was prepared by the procedure of Example 52, utilizing 1.75 grams of (2-phenyl-2H-1,2,3-triazol-2-yl)methylamine, 3.3 grams of 2-methylthiobenz(cd)indole hydriodide, and 100 ml of ethanol. The yield was 2.9 grams and the compound melted at 212° C.-215° C. with decomposition.

EXAMPLE 73

N-Methyl-N-(2-(2-pyridinyl)ethyl)benz(cd)indol-2-amine fumarate

The title compound was prepared by the procedure of Example 52, an equivalent of N-methyl-(2-(2-pyridinyl)ethyl)amine replacing the 2-pyridinylmethylamine. The yield of product was 3.5 grams, and the melting point was 144° C.-146° C. with decomposition.

EXAMPLE 74

N-(3-(1H-imidazol-1-yl)-2-hydroxypropyl)benz(cd)indol-2-amine and its difumarate salt The starting amine, 1-amino-3-(1H-imidazol-1-yl)propane-2-ol, was prepared as follows: a mixture consisting of 10.0 garms N-(2,3-epoxypropyl) phthalimide, 3.6 grams of imidazole, and 50 ml of acetonitrile was stirred and heated under reflux for 16 hours. 100 ml of acetonitrile was added, and the reaction mixture then cooled at −10° C. The precipitate of 1-(1H-imidazol-1-yl)-3-(N-phthalimido)propan-2-ol was collected, washed with acetonitrile, and dried. Treatment of a latter compound with hydrazine in boiling ethanolic solution than gave the desired starting amine as a clear viscous oil which was used directly in the following synthesis.

A mixture consisting of 2.5 grams of 1-amino-3-(1H-imidazol-1-yl)propan-2-ol, 5.0 grams of 2-methylthiobenz(cd)indole hydriodide and 300 ml of ethanol was stirred and heated under reflux for 16 hours. The reaction conditions and workup of Example 13 were followed. A portion of the difumarate salt was reserved; it melted at 182° C.-184° C. with decomposition. The remainder of the difumarate salt was dissolved in water and the solution made basic with 5N NaOH solution. The yellow precipitate of N-(3-(1H-imidazol-1-yl)-2-hydroxypropyl)benz(cd)indol-2-amine was collected, washed with water, and dried in vacuo at room temperature. The yield was 1.6 grams; mp 98° C.-100° C. with decomposition.

EXAMPLE 75

N-(2-(4-(1H-imidazol-1-yl)butyl)benz(cd)indol-6-yl)-4-methylbenzenesulfonamide monoacetate The starting material, N-((2-thiobenz(cd)indol-6-yl)-4-methyl)benzenesulfonamide was prepared by the following route: 6-aminobenz(cd)indol-2-one and p-toluenesulfonyl chloride in pyridine gave the corresponding 6-(4-methylphenyl)sulfonamide derivative of benz(cd)indol-2-one, which upon treatment with $P_2S_5$ in refluxing pyridine gave the desired starting material, mp 265° C.-258° C. with decomposition.

The reaction of the latter compound (3.5 grams) with 4-(1H-imidazol-1-yl)butylamine (1.4 grams) in refluxing ethanol (150 ml) in the presence of mercuric acetate (3.2 grams) gave, after four hours of refluxing, a black slurry which was clarified hot. 20 ml of 1N NaOH solution was then added, and the solution taken to dryness in vacuo. Purification of the crude free base was carried out by the chromatographic procedure of Example 46. The purified free base was dissolved in 3 ml of glacial acetic acid, and the excess acetic acid was removed in vacuo. The reddish-orange gum remaining was triturated with a 1:1 mixture of ethylacetate:ethanol—crystallization soon commenced. After cooling at −10° C., the mixture was filtered, washed with a little of the solvent mixture, and dried in vacuo. The yield of the title compound was 0.45 gram; mp 153° C.-156° C. with decomposition.

EXAMPLE 76

N-(3-(4-pyridinyl)butyl)benz(cd)indol-2-amine

The title compound was prepared by the procedure of Example 55, utilizing 3.1 grams of 3-(4-pyridinyl)-butanamine, 3.9 grams of benz(cd)indol-2-thiol, 6.4 grams of mercuric acetate, and 300 ml of ethanol. Chloroform (200 ml) was utilized as the partitioning solvent in place of dichloromethane. When the chloroform was being removed in vacuo, crystallization of the title compound suddenly occurred. The precipitate was collected, washed with a little chloroform, and dried. The yield was 3.9 grams; mp 220° C.–221° C. with decomposition.

EXAMPLE 77

N-(2-(1H-imidazol-4-yl)ethyl)benz(cd)indol-2-amine

The preparation of the subject compound was carried out by the procedure of Example 52, utilizing 1.7 grams of 2-(1H-imidazol-4-yl)ethanamine in place of 2-pyridinylmethylamine. The crude reaction product was purified by recrystallization from 150 ml of 33% ethanol; yield, 1.4 grams; mp 255° C.–257° C. dec.

EXAMPLE 78

6,8-Dichloro-N-(3-(1H-imidazol-1-yl)butyl)benz(cd)indol-2-amine dihydrochloride

The product of Example 33 (0.53 gram) was dissolved in 150 ml of ethanol, and 1.5 ml of 2.3N ethanolic hydrogen chloride. The solution was concentrated to about 50 ml volume and diluted with 100 ml of diethyl ether. The precipitate of the title compound was collected, washed with diethyl ether, and dried; yield, 0.49 gram; mp 257° C.–259° C. with decomposition.

EXAMPLE 79

N-(3-(3-Pyridinyl)butyl)benz(cd)indol-2-amine

The subject compound was prepared by the procedure of Example 55, utilizing 2.3 grams of 3-(3-pyridinyl)butanamine in place of 2-pyridinylmethylamine. The residue left after removal of the dichloromethane was triturated with acetone, effecting crystallization. The yield was 1.9 grams; mp 160° C.–163° C. with decomposition.

EXAMPLE 80

2-Methyl-3-(3-pyridinyl)propylbenz(cd)indol-2-amine sesqui-fumarate

The title compound free base was prepared by the procedure of Example 55, utilizing 3.1 grams of 2-methyl-3-(3-pyridinyl)propanamine, 3.9 grams of benz(cd)indol-2-thiol, 6.4 grams of mercuric acetate, and 250 ml of ethanol. Purification was effected by the chromatographic procedure of Example 46. The 5.0 grams of free base was dissolved in 200 ml of acetone and added to a stirred boiling solution of 4.2 grams of fumaric acid in 840 ml of acetone. The yellow precipitate was collected, washed with acetone, and dried. The yield of title compound was 3.8 grams; mp 154° C.–156° C. with decomposition.

EXAMPLE 81

N-(2-Ethyl-2-(1H-imidazol-1-yl)methyl)butylbenz(cd)indol-2-amine sesqui-fumarate The subject compound was prepared by the method of Example 55, employing 0.75 grams of 2-ethyl(2-(1H-imidazol-1yl)-1-ylmethyl)butanamine, 0.84 grams of benz(cd)indol-2-thiol, 1.43 grams of mercuric acetate, and 100 ml of ethanol. The yield was 1.70 grams, and the mp was 179° C.–182° C. with decomposition.

EXAMPLE 82

6,8-Dichloro-N-(3-(1H-imidazol-1-yl)-2-methylpropyl)-benz(cd)indol-2-amine and its sesqui-fumarate The title compound was prepared by the method of Example 55, utilizing 7.6 grams of 6,8-dichlorobenz(cd)indol-2-thiol, 4.2 grams of 3-(1H-imidazol)-2-methylpropanamine, 9.5 grams of mercuric acetate, and 300 ml of ethanol. The crude product was triturated with acetone and the mixture cooled at 5° C. The crystals of free base were collected, washed with diethyl ether and dried; mp 180° C.–181° C.

The solution of 1.5 grams of the above free base in 100 ml of hot acetone was added to a stirred solution of 1.0 gram of fumaric acid in 100 ml of hot acetone. Orange crystals of the sesqui-fumarate salt were collected, washed with acetone and dried; yield, 2.1 grams; mp 131° C.–132° C.

EXAMPLE 83

6,8-Dichloro-N-(7-(1H-imidazol-1-yl)heptyl) benz(cd)indol-2-amine dihydrochloride The free base of the title compound was prepared by the method of Example 55, utilizing 5.4 grams of 7-(1H-imidazol-1-yl)heptanamine, 7.6 grams of 6,8-dichlorobenz(cd)indol-2-thiol, 9.5 grams of mercuric acetate, and 500 ml of ethanol. A solution of 2.5 grams of the free base in 100 ml warm ethanol was treated with 30 ml of 2.3 N ethanolic hydrogen chloride. The resultant mixture was taken to dryness in vacuo, and the residual syrup boiled up in 400 ml of acetone. Cooling at room temperature gave 1.9 grams of the title compound mp 198° C.–201° C.

EXAMPLE 84

6,8-Dichloro-N-(4-(3-pyridinyl)butyl)benz(cd)indol-2-amine and its fumarate salt The subject compound free base was prepared by the procedure of Example 55, utilizing 4.5 grams of 4-(3-pyridyl)butanamine, 7.6 grams of 6,8-dichlorobenz(cd)indol-2-thiol, 9.5 grams of mercuric acetate, and 400 ml of ethanol. Recrystallization from ethanoldiethyl ether gave 4.0 grams of the pure free base, mp 143.5° C.–144.5° C.

A solution of 2.5 grams of the free base in 100 ml acetone was added to a stirred boiling solution of 2.0 grams of fumaric acid in 200 ml acetone. The fumarate salt was collected, washed with acetone, and dried; yield, 2.5 grams; mp 187° C.–188° C. with decomposition.

EXAMPLE 85

6-Bromo-N-(3-(1H-imidazol-1-yl)-2-methylpropyl)-benz(cd)indol-2-amine dihydrochloride The free base of the title compound was prepared by the procedure of Example 55, employing 2.8 grams of 3-(1H-imidazol-1-yl)-2-methylpropanamine, 5.3 grams of 6-bromobenz(cd)indol-2-thiol, 6.45 grams of mercuric acetate, and 500 ml of ethanol. The crude free base was purified by the chromatographic procedure of Example 46, 5.5 grams of product being obtained. This was converted to the dihydrochloride salt by treatment with excess 2.3N ethanolic hydrogenchloride, followed by precipitation with acetone. The yield was 1.2 grams and the mp 180° C. with decomposition.

EXAMPLE 86

6-Bromo-N-(4-(3-pyridinyl)butyl)benz(cd)indol-2-amine dihydrochloride

The free base of the title compound was prepared by the procedure of Example 55, utilizing 3.0 grams of 4-(3-pyridyl)butanamine, 5.3 grams of 6-bromobenz(cd)indol-2-thiol, 6.4 grams of mercuric acetate, and 500 ml of ethanol. The crude free base was purified by the chromatographic procedure of Example 46. It was then dissolved in 100 ml of hot acetone and added to a mixture of 25 ml of 3.4N ethanolic hydrogen chloride and 50 ml of ethanol. Partial evaporation of the solution gave yellow crystals of the title compound; yield 6.5 grams; mp 241° C.-244° C.

EXAMPLE 87

6-Fluoro-N-(1H-imidazol-1-yl)propyl)benz(cd)indol-2-amine

The title compound was prepared by the procedure of Example 55, utilizing 1.3 grams of 3-(1H-imidazol-1-yl)propanamine, 2.0 grams of 6-fluorobenz(cd)indol-2-thiol, 3.2 grams of mercuric acetate, and 50 ml of ethanol. Purification of the crude product by recrystallization from acetone gave 0.92 gram; mp 159° C.-160° C.

EXAMPLE 88

N-Benz(cd)indol-2-yl-N-(4-(1H-imidazol-1-yl)butyl)-pentanamide

A solution consisting of 2.3 grams of N-(4(1H-imidazol-1-yl)butyl)benz(cd)indol-2-amine (the free base of the compound of Example 18) and 0.3 gram of 4-dimethylaminopyridine in 200 ml of dichloromethane was treated with 1.8 grams of n-pentanoic anhydride by the conditions of Example 45. Recrystallization of the crude product from acetone-hexane gave 0.55 gram of the title compound; mp 110° C.-112° C.

EXAMPLE 89

N-(2-((2-pyridinylmethyl)thio)ethyl)benz(cd)indol-2-amine fumarate

The amine, 2-(2-pyridinylmethyl)thio)ethanamine, was prepared as described in the *Eur. J. Med. Chem—Chim Therap.* 1985-20 (5) pp. 403-407.

Two and a half grams of the above amine, 5.0 grams of 2-methylthiobenz(cd)indol hydriodide, and 300 ml of ethanol were combined and the reaction carried out by the procedure of Example 52. The crude base was dissolved in 200 ml of acetone and added to a stirred boiling solution of 4.0 grams of fumaric acid in 800 ml of acetone. The yield of title compound was 3.8 grams; mp 151° C.-152° C. with decomposition.

EXAMPLE 90

N-(3-(1H-imidazol-1-yl)-1-methylpropyl)benz(cd)indol-2-amine difumarate

The subject compound was prepared by the method of Example 52, utilizing 4.5 grams of 3-(1H-imidazol-1-yl)-1-methylpropanamine, 6.0 grams of 2-methylthiobenz(cd)indole hydriodide, and 400 ml of ethanol. A portion of the isolated free base was converted to the difumarate salt which melted at 195° C.-197° C. with decomposition.

EXAMPLE 91

N-(3-(4-Methyl-2-thiazolyl)propyl)benz(cd)indol-2-amine fumarate

The subject compound was prepared by the method of Example 55, utilizing 1.0 gram of 3-(4-methyl-2-thiazolyl)propanamide, 1.0 gram of benz (cd)indol-2-thiol, 2.0 grams of mercuric acetate, and 50 ml of ethanol. The crude free base was purified by the chromatographic procedure of Example 46, and converted to the title compound by treatment with fumaric acid in boiling acetone. The yield was 0.95 gram; mp 172° C.-173° C. with decomposition.

EXAMPLE 92

N-Benz(cd)indol-2-yl-N-(4-(1H-imidazol-1-yl)butyl)-heptanamide

The subject compound was prepared by the method of Example 45, utilizing 4.0 grams of N-(4-(1H-imidazol-1-yl)butyl)benz(cd)indol-2-amine (the free base of the compound of Example 18), 3.7 ml of n-heptanoic anhydride, and 50 ml of the dichloromethane. The crude product was recrystallized from diethylether to yield 2.2 grams of the title compound; mp 82° C.-84° C.

EXAMPLE 93

N-Benz(cd)indol-2-yl-N-(4-(1H-imidazol-1-yl)butyl)-hexanamide

The title compound was prepared by the procedure of Example 45, utilizing 3.0 grams of N-(4-(1H-imidazol-1-yl)benz(cd)indol-2-amine, 2.5 ml of hexanoic anhydride, and 50 ml of dichloromethane. The crude product was recrystallized from tetrahydrofuran to yield 0.23 gram of the title compound, mp 110° C.-111° C.

EXAMPLE 94

N-Benz(cd)indol-2-yl-N-(4-(3-pyridinyl)butyl)-3-trifluoromethylbenzamide

A solution of 5.0 grams of N-(4-(3-pyridinyl)butyl)-benz(cd)indol-2-amine in 50 ml of pyridine was stirred as 2.5 ml of 3-trifluoromethylbenzoyl chloride was slowly added. The reaction mixture was stirred at room temperature for 18 hours, and drowned onto 500 ml of ice. The precipitate was collected, washed with water and dried. Recrystallization from chloroform-hexane gave 3.95 grams of the title product, mp 122° C.-123° C.

EXAMPLE 95

N-(4-(3-Pyridinyl))benz(cd)indol-2-amine, hydriodide salt and sesqui-fumarate salt A mixture of 17.0 grams of 4-(3-pyridinyl)butanamine, 32.7 grams of 2-methylthiobenz(cd)indole hydriodide, and 200 ml of ethanol was stirred and heated under reflux for 18 hours. Cooling to room temperature gave a yellowish precipitate of the hydriodide salt, which was collected, washed with ethanol and dried. The yield was 37.9 grams and the mp as 210° C.-212° C.

A portion of the hydriodide salt was converted to the free base by shaking with 10N NaOH solution, and extraction with dichloromethane. 3.6 grams of the base was dissolved in 200 ml of acetone and added to a stirred solution of 3.5 grams of fumaric acid in 800 ml of acetone. The yield of the sesqui-fumarate salt obtained after drying was 2.7 grams, mp 98° C.-100° C.

EXAMPLE 96

N-Benz(cd)indol-2-yl-N-(4-(1H-imidazol-1-yl)butyl-2-methoxybenzamide

A solution of 3.95 grams of N-(4-(1H-imidazol-1-yl)butyl)benz(cd)indol-2-amine and 0.1 gram of 4-dimethylaminopyridine was treated with 3.0 grams of 2-methoxybenzoyl chloride. The mixture was stirred at room temperature for 16 hours and then drowned onto 500 grams of ice. The precipitate was collected, washed with water, and dried. Recrystallization from dichloromethane-hexane gave 3.1 grams of the title compound, mp 146° C.-147° C.

EXAMPLE 97

N-Benz(cd)indol-2-yl-N-(4-(1H-imidazol 1-yl)butyl)-3-trifluoromethylbenzamide

Following the procedure of Example 96, but replacing the 2-methoxybenzoyl chloride by 3.5 grams of 3-trifluoromethylbenzoyl chloride, there was obtained 4.3 grams of the title compound, mp 165° C.-167° C.

EXAMPLE 98

N-Benz(cd)indol-2-yl-N-(4-(1H-imidazol-1-yl)butyl)-benzamide

Following the procedure of Example 96, but replacing the 2-methoxybenzoyl chloride by 2.0 ml of benzoyl chloride, there was obtained 0.9 gram of the title compound, mp 139° C.-140° C.

EXAMPLE 99

N-Benz(cd)indol-2-yl-N-(4-1H-imidazol-1-yl)butyl)-2-furancarboxamide

The procedure of Example 96 was followed, 1.6 ml of 2furancarbonyl chloride replacing the 2-methoxybenzoyl chloride. The yield of title compound was 0.5 gram and the mp was 92° C.-93° C.

EXAMPLE 100

N-Benz(cd)indol-2-yl-N-(4-(1H-imidazol-1-yl)butyl)-4-fluorobenzamide

The procedure of Example 96 was followed, 2.0 ml of 4-fluorobenzoyl chloride replacing the 2-methoxybenzoyl chloride. The yield of title compound was 1.0 gram; mp 109° C.-110° C.

EXAMPLE 101

N-Benz(cd)indol-2-yl-N-(4-(1HH-imidazol-1-yl)butyl)-4-methylbenzamide

The procedure of Example 96 was followed, 2.2 ml of 4-methylbenzoyl chloride replacing the 2-methoxybenzoyl chloride. The yield of title compound was 0.25 gram; mp 134° C.-135° C.

EXAMPLE 102

N-Benz(cd)indol-2-yl-N-(4-(1H-imidazol-1-yl)butyl)-2-thiophenecarboxamide

The procedure of Example 96 was followed, 1.7 ml of 2-thiophenecarbonyl chloride replacing the 2-methoxybenzoyl chloride. The yield of title compound was 1.0 gram; mp 76° C.-80° C.

EXAMPLE 103

N-Benz(cd)indol-2-yl-3,4-dichloro-N-(4-(1H-imidazol-1-yl)butyl)benzamide

The procedure of Example 96 was followed, 2.2 grams of 3,4-dichlorobenzoyl chloride replacing the 2-methoxybenzoyl chloride. The yield of title compound was 2.1 grams; mp 138° C.-141° C.

EXAMPLE 104

N-(3-(1H-imidazol-1-yl)propyl-N-(n-octyl))benz(cd)indol-2-amine difumarate

The requisite starting amine was prepared as follows: reaction of n-octanoic acid and 1,1'-carbonyldi(1-imidazole) in tetrahydrofuran solution with 3-(1H-imidazol-1-yl)propanamine gave N-3-(1H-imidazolyl) propyl-n-octanamide, which upon reduction with $BH_3$ in tetrahydrofuran solution gave N-(3-(1H-imidazol-1-yl) propyl-N-(n-octyl))amine.

A mixture of 3.2 grams of the above amine, 2.5 grams of benz(cd)indol-2-thiol, 4.15 grams of mercuric acetate, and 300 ml of ethanol was stirred and heated under reflux for 52 hours. The crude free base was isolated by the procedure of Example 16, and purification by the chromatographic procedure of Example 46. The yield of purified base was 3.2 grams. It was dissolved in 200 ml of acetone and added to a stirred refluxing solution of 2.0 grams of fumaric acid in 200 ml of acetone. The acetone was then removed in vacuo, and the residual syrup recrystallized from ethanol to yield 4.15 grams of the title compound, mp 149° C.-151° C.

EXAMPLE 105

N-(4-(1H-imidazol-1-yl)butoxy)benz(cd)indol-2-amine

The starting amine was prepared as follows: the reaction of N-hydroxyphthalimide and 1,4-dibromobutane in dimethylformamide solution in the presence of triethylamine gave N-(4-bromobutoxy)phthalimide which upon reaction with the sodium salt of imidazole in dimethylformamide solution gave N-(4-(1H-imidazol-1-yl)butoxy)phthalimide. Treatment of the latter compound with hydrazine in ethanol solution then gave the desired amine, 4-(1H-imidazol-1-yl) butoxyamine.

A mixture consisting of 1.6 grams of the latter amine, 1.9 grams of benz(cd)indol-2-thiol, 3.3 grams of mercuric acetate, and 150 ml of ethanol was stirred and heated under reflux by the conditions of Example 55. The crude product was purified by the chromatographic procedure of Example 46. The resultant orange syrup was recrystallized from ethyl acetate to yield 1.15 grams of orange crystals of the title compound, mp 126°-128° C.

EXAMPLE 106

N-(3-(1H-imidazol-1-yl)propoxy)benz(cd)indol-2-amine

The starting amine, 3-(1H-imidazol-1-yl)propoxyamine, was prepared by the procedure described in Example 104, 1,3-dibromopropane replacing the 1,4-dibromobutane.

A mixture consisting of 2.33 grams of 3-(1H-imidazol-1-yl)propoxyamine, 2.84 grams of benz(cd)indol-2-thiol, 4.9 grams of mercuric acetate, and 150 ml of ethanol as stirred and heated under reflux by the conditions of Example 55. The crude product was purified by the chromatographic procedure of Example 46. The resultant orange syrup was recrystallized from ethyl acetate-hexane to give 2.3 grams of the title compound; mp 102° C.–104° C.

EXAMPLE 107

N-(4-(1H-imidazol-1-yl)butyl)benz(cd)indol-2-amine dimethiodide

A solution of 5.2 grams of N-(4-(1H-imidazol-1-yl) butyl)benz(cd)indol-2-amine (free base of the compound of Example 18) in 200 ml of acetone was treated with 3.0 ml of methyliodide, and allowed to stand at room temperature. An orange precipitate formed slowly. After three days, the precipitate was collected, washed with acetone, and dried. The yield of the title compound was 4.0 grams; mp 225° C.–230° C. with decomposition.

EXAMPLE 108

N-(4-(4-Pyridinyl)butyl)benz(cd)indol-2-amine hydriodide

A mixture consisting of 3.3 grams of 4-(4-pyridinyl)-butanamine, 6.5 grams of 2-methylthiobenz (cd)indole hydriodide, and 200 ml of ethanol. Cooling to room temperature failed to effect precipitation, so that solution was concentrated to 100 ml volume and cooled at −10° C. The precipitate that formed was collected, washed with ethanol, and dried. The yield of title compound was 6.1 grams; mp 197° C.–199° C. with decomposition.

EXAMPLE 109

N-(1-(4-Chlorophenyl)-2-(1H-1,2,4-triazol-1-yl)ethyl)-benz(cd)indol-2-amine fumarate The starting amine, 1-(4-chlorophenyl)-2-(1H-1,2,4-triazol-1-yl) ethylamine, was prepared by the reductive amination of 1-(2-(4-chlorophenyl)-2-oxoethyl)-1H-1,2,4-triazole with $NaBH_3CN$- ammonium acetate in methanol solution.

A mixture of 2.9 grams of the above amine, 4.2 grams of 2-methylthiobenz(cd)indole hydriodide, and 40 ml of ethanol was stirred and heated under reflux, utilizing the reaction conditions of Example 55. The crude free base was dissolved in 50 ml of acetone and added to a hot solution of 1.0 gram of fumaric acid in 200 ml of acetone. Cooling gave a precipitate of the title compound, which was collected and dried; yield 0.7 gram; mp 195° C.–197° C. with decomposition.

EXAMPLE 110

N-(2-(2-Pyridinyloxy)ethyl)benz(cd)indol-2-amine fumarate

A mixture consisting of 3.0 grams of 2-(2-pyridinyloxy) ethylamine, 6.5 grams of 2-methylthiobenz(cd)indole hydriodide, and 150 ml of ethanol was stirred and heated under reflux, utilizing the conditions of Example 16. The crude free base (weight, 7.1 grams) was dissolved in 20 ml of acetone and added to a stirred boiling solution of 5.5 grams of fumaric acid in 1200 ml of acetone. After cooling the precipitate of the title compound was collected, washed with acetone, and dried; yield, 7.6 grams; mp 184° C.–185° C. with decomposition.

EXAMPLE 111

N-(3-(1H-Pyrazol-1-yl)propyl)-benz(cd)indol-2-amine fumarate

A mixture consisting of 2.8 grams of 3-(1H-pyrazol-1-yl)propanamine, 3.7 grams of benz(cd)indol-2-thiol, 7.0 grams of mercuric acetate, and 400 ml of ethanol was stirred and heated under reflux, by the conditions of Example 55. The isolated crude free base, weight 4.0 grams, was dissolved in 150 ml of acetone and added to stirred boiling solution of 3.5 grams of fumaric acid in 800 ml of acetone. After cooling, the precipitate of the title compound was collected, washed with acetone, and dried. The yield was 4.1 grams; mp 178° C.–180° C. was decomposition.

EXAMPLE 112

N-(2-(3-Pyridinyl)ethyl)benz(cd)indol-2-amine sesqui-fumarate

A mixture consisting of 2.6 grams of 2-(3-pyridyl) ethylamine, 6.5 grams of 2-methylthiobenz (cd)-indole hydriodide, and 250 ml of ethanol was stirred and heated under reflux, by the conditions of Example 52. The isolated crude yield, weight 5.6 grams, was dissolved in 200 ml of acetone and added to a stirred boiling solution of 5.0 grams of fumaric acid in 1200 ml of acetone. After cooling, the precipitate of the title compound was collected, washed with acetone, and dried. The yield was 6.4 grams; mp 170° C.–171° C. with decomposition.

EXAMPLE 113

N-((3-Pyridinyl)methyloxyethyl)benz(cd)indol-2-amine fumarate

The starting amine, (3-pyridinyl)methyloxyethylamine, was prepared by the following procedure: reaction of the sodium salt of 3-pyridinylmethanol and chloracetonitrile in dimethylformamide gave 2-(3-pyridinyloxy)acetonitrile, which, upon reduction with borane in tetrahydroduran solution, gave the desired amine.

A mixture of 2.2 grams of (3-pyridinyl)-methyloxyethylamine, 2.6 grams of benz(cd)indol-2-thiol, 4.6 grams of mercuric acetate, and 100 ml of ethanol was stirred and heated under, reflux, by the conditions of Example 55, and the crude base purified by the chromatographic procedure of Example 46. The yield of purified base as 3.0 grams. It was dissolved in 50 ml of acetone, and the solution added to a stirred boiling solution of 2.8 grams of fumaric acid in 300 ml of acetone. Cooling at 5° C. gave the title compound; yield, 2.75 grams; m; 165° C.–168° C.

EXAMPLE 114

N-(3-(1H-imidazol-1-yl)propyl)-6-methylsulfonyl-benz(cd)indol-2-amine

The reaction of molecular equivalents of 6-methylsulfonylbenz(cd)indol-2-thiol, 3-(1H-imidazol-1-yl)propanamine, mercuric acetate, and sufficient refluxing ethanol to permit stirring, by the procedure of Example 55 gives the title compound.

EXAMPLE 115

5-Methoxy-N-(4-(4-pyridinyl)butyl)benz(cd)indol-2-amine

The reaction of 4-(4-pyridinyl)butanamine and 5-methoxy-2-methylthiobenz(cd)indole hydriodide in refluxing ethanol gives the hydriodide salt of the title compound, which upon treatment with alkali hydroxide solution yields the free base.

EXAMPLE 116

N-(3-(1H-imidazol-1-yl)propyl)-2-aminobenz(cd)indol-6-carbonitrile

A mixture consisting of 9.9 grams of 6-bromobenz(cd)indol-2one, 5 grams of cuprous cyanide and 100 ml of dry dimethylformamide was stirred and heated under reflux for 20 hours. The hot mixture was filtered, and the filtrate, after cooling, gave 3.2 grams of 6-cyanobenz (cd)indol-2-one, m.p. 315° C., with decomposition. Treatment of the latter compound with 2.2 grams of phosphorous pentasulfide in 100 ml of refluxing pyridine for 18 hours, concentrating to dryness and treating with water gave 2.8 grams of crude 6-cyanobenz(cd)indol-2-thione. A portion recrystallized from acetic acid melted above 320° C. 2.8 grams of 6-cyanobenz(cd)indol-2-thione, 1.7 grams of 3-(1H-imidazolyl)propylamine, 4.2 grams of mercuric acetate, 100 ml of ethanol and 20 ml of dimethylformamide were combined and heated under reflux for 7 hours. The hot reaction mixture was filtered through diatomaceous earth, and the cake washed with 25 ml of hot dimethylformamide. The filtrate was then concentrated to dryness in vacuo. The residue was shaken with 50 ml of 5N sodium hydroxide and the mixture extracted three times with 100 ml portions of chloroform. The combined chloroform extracts were dried over sodium sulfate and the chloroform removed in vacuo. The yellow residue was recrystallized from methanol, yielding 1.9 g of N-(3-(1H-imidazol-1-yl)propyl)-2-aminobenz(cd)indol-6-carbonitrile melting at 214°C.-215° C. and analyzing as the ¼ hydiate.

Analysis:

Calculated for $C_{18}H_{15}N_5\frac{1}{4}H_2O$: C, 70.68; H, 5.11; N, 22.90.

found: C, 70.95; H, 5.11; N, 22.74.

EXAMPLE 117

N-(3-(1H-imidazol-1-yl)propyl)-2-aminobenz(cd)indol-6-carbonamide

The compound of Example 115 is dissolved in 20 parts of concentrated sulfuric acid, and stirred as 5 parts of water is added carefully. After six hours, the solution is drowned into 500 parts of ice-water. Neutralization with alkali hydroxide then yields the title compound.

EXAMPLE 118

8-Methyl-N-(4-(3-pyridinyl)butyl)indol-2-amine hydriodide

To a solution of 2.6 grams of 4-(3-pryidinyl butylamine in 75 ml of ethanol, 5.1 grams of 8-methyl-2-methylthiobenz(cd)indole hydriodide was added. The mixture was then stirred and heated under reflux for 16 hours. The hot reaction mixture was clarified and the filtrate cooled at −10° C., yielding 4.75 grams of 8-methyl-N-(4-(3-pyridinyl)butyl)benz(cd)indol-2-amine hydriodide, m.p. 175°-176° C. with decomposition.

Analysis:

Calculated for $C_{21}H_{21}N_3.HI$: C, 56.89; H, 5.00; N, 9.47; I, 28.69.

Found: C, 56,57, H, 4.80; N, 9.18; I, 28.30.

EXAMPLE 119

6-Benzyl-N-(3-(1H-imidazol-1-yl)butyl)benz(cd)indol-2-amine

The Wolff-Kishner-Huang Minlon reductive procedure is applied to 6-benzoylbenz(cd)indol-2-one to yield 6-benzylbenz(cd)indol-2(1H)-one which is converted to 6-benzylbenz(cd)indol-2-thiol by $P_2S_5$ in refluxing pyridine. The reaction of the latter compound with 3-(1H-imidazol-1-yl)butanamine and mercuric acetate in refluxing ethanol, under the conditions of Example 55, leads to the title compound.

EXAMPLE 120

4-Dimethylamino-N-(3-(3-pyridinyl)propyl)benz(cd)indol-2-amine

The reaction of equivalent molar quantities of 3-(3-pyridinyl)propanamine, 4-dimethylaminobenz(cd)indol-2thiol, and mercuric acetate in refluxing ethanol, under the conditions of Example 55 leads to the formation of the title compound.

EXAMPLE 121

6-(N-Piperidino)-N-(2-(4-pyridinyl)ethyl)benz(cd)indol-2-amine

The preparation of the title compound is accomplished by the procedure of Example 119, 6-N-piperidino)benz(cd)indol-2-thiol replacing the 4-dimethylamino analog.

EXAMPLE 122

5-Hydroxy-N-(4-(4-pyridinyl)butyl)benz(cd)indol-2-amine

The compound of Example 114 is dissolved in 57% hydriodic acid, and the solution stirred at reflux. Removal of the hydriodic acid in vacuo, followed by neutralization with alkali hydroxide solution leads to the title compound.

EXAMPLE 123

6-Methylthio-N(3-(4-pyridinyl)propyl)benz(cd)indol-2-amine

Chlorosulfonation of benz(cd)indol-2-(1H-one yields the 6-sulfonylchloride derivative, which upon treatment with zinc dust in acetic acid-hydrochloric acid solution, yields 6-mercaptobenz(cd)indol-2-(1H)-one. Treatment with dimethyl sulfate in alkaline solution leads to 6-methylthiobenz(cd)indol-2-(1H)-one, which on heating with $P_2S_5$ in pyridine yields 6-methylthiobenz(CD)indol-2-thiol. The reaction of the latter compound with molar equivalents of 3-(4-pyridinyl)-propanamine and mercuric acetate in ethanol, under the conditions of Example 55, leads to the title compound.

EXAMPLE 124

6-Diethylaminomenthyl-N-(3-(1H-imidazol-1-yl)propyl)benz(cd)indol-2-amine

6-Bromobenz(cd)indol-2-(1H)-one is treated with ethyl chloroformate in alkaline solution to yield the N-carbethoxy derivative. Successive reactions with magnesium, formaldehyde, and 48% hydrobromic acid leads to 6-bromomethylbenz(cd)indol-2(1H)-one, which on treatment with diethylamine yields the 6-diethylaminomethyl derivative. Treatment with $P_2S_5$ in refluxing pyridine leads to 6-diethylaminomenthylbenz(cd)indol-2-thiol, which on reaction with molar equivalents of 3-(1H-imidazol-1yl)propanamine and mercuric acetate in refluxing ethanol, under the conditions of Example 55, leads to the preparation of the title compound.

EXAMPLE 125

N-(3-(1H-imidazol-1-yl)propyl)-N-phenylbenz(cd)indol-2-amine

The reaction of 1,1'-carbonyldiimidazole and 3-(1e,uns/H/ -imidazol-1yl)propanoic acid in tetrahydrofuran solution, followed by treatment with aniline leads to the formation of N-phenyl-3-(1H-imidazol-1-yl)propanamide. Reduction with borane in tetrahydrofuran solution then gives N-phenyl-3-(1H-imidazol-1-yl)propanamide. Reduction with borane in tetrahydrofuran solution then gives N-phenyl-3-(1H-imidazol-1-yl)propanamide. The latter compound with molar equivalents of benz(cd)indol-2-thiol and mercuric acetate in refluxing ethanol leads tot eh formation of the title compound, under the conditions of Example 55.

EXAMPLE 126

N-Cyclohexyl-N-((3-pyridinyl)propyl)benz(cd)indol-2-amine

The reaction of 3-(3-pyridinyl)propanamine and cyclohexanone in methanol in the presence of $NaBH_3CN$ leads to the preparation of N-cyclohexyl-3-(3-pyridinyl)propanamine. The latter compound, upon reaction with molar equivalents of benz(cd)indol-2-thiol and mercuric acetate in refluxing ethanol under the conditions of Example 55 leads to the title compound.

EXAMPLE 127

N-(3-(1H-imidazol-1-yl)propyl)-N-(2-methoxyethyl)-benz(cd)indol-2-amine

The reaction of 2-methoxyacetyl chloride and 3-(1H-imidazol-1-yl)propanamine in the presence of triethylamine leads to the formation of N-(3-(1H-imidazol-1-yl)propyl)-2-methoxyacetamide, which by reduction with borane gives N-(3-(1H-imidazol-1-yl)propyl)-2-methoxyethylamine. The latter amine reacts with molar equivalents of benz(cd)indol-2-thiol and mercuric acetate in refluxing ethanol, under the conditions of Example 55 to yield the title compound.

EXAMPLE 128

N-(3-(1H-imidazol-1-yl)propyl)-N-(2-hydroxyethyl)-benz(cd)indol-2-amine

Treatment of the compound of Example 127 with refluxing 48% HBr solution results in the demethylation of the compound. Removal of the HBr solution in vacuo and neutralization with alkali hydroxide solution yields the title compound.

EXAMPLE 129

N-(3-Dimethylaminopropyl)-N-(3-(1H-imidazol-1-yl)propyl)benz(cd)indol-2-amine

3(1H-imidazol-1-yl)propanoic acid is converted to its acid chloride which upon reaction with 3-dimethylaminopropylamine leads to N-(3-dimethylaminopropyl)-3-(1H-imidazol-1-yl)propanamide. Reduction with borane in tetrahydrofuran solution then gives N-(3-dimethylaminopropyl-N-3-(1H-imidazol-1yl))-propanamine. Treatment of the latter compound with molar equivalents of benz(cd)indol-2-thiol and mercuric acetate in refluxing ethanol under the conditions of Example 55 then leads to the title compound.

EXAMPLE 130

N-(4(1H-imidazol-1-yl)-2-butyn-1-yl)benz(cd)indol-2-amine

The sequential reaction of 1,4-dichloro-2-butyne with potassium phthalimide and then the sodium salt of imidazole leads to the formation of N-(4-(1H-imidazol-1yl)2-butyn-1-yl)phthalimide, which upon treatment with hydrazine in boiling ethanol leads to 4-(1H-imidazol-1yl)-2-butyn-1-ylamine. Reaction of the latter compound with 2-methylthiobenz(cd)indole hydriodide in ethanol solution, by the conditions of Example 52 leads to the hydriodide of the title compound which is converted to the free base by treatment with alkali hydroxide solution.

EXAMPLE 131

N-(2-(2-(1H-imidazol-1l)ethylsulfonyl)ethyl-benz(cd)indol-2-amine

The sequential reaction of bis(2-bromethyl)sulfone with potassium phthalimide and then the sodium salt of imidazole leads to the formation of N-(2-(2-(1H-imidazol-1-yl)ethylsulfonyl)ethyl)phthalimide, which upon treatment with hydrazine in boiling ethanol leads to 2-(2-(1H-imidazol-1yl)ethylsulfonyl)ethanamine. Reaction of the latter amine with 2-methylthiobenz(cd)indole hydriodide in ethanol solution, by the conditions of Example 52 leads to the formation of the hydriodide of the title compound, convertible to the free base by treatment with alkali hydroxide solution.

EXAMPLE 132

N-(3-(2-(3-Pyridinymethyl)amino)propyl)benz(cd)indol-2-amine

Treatment of 3-pyridinylmethylamine with N-carbobenzyloxyglycine by the carbonyl(di-1-imidazole) procedure, followed by catalytic hydrogenalysis of the carbobenzyloxy group leads to the formation of N-(3-pyridinymethyl)glycinamide. Reduction of this latter compound with borane in tetrahydrofuran solution then gives N-(3-pyridinylmethyl)ethane-1,2-diamine. This compound, upon reaction with 2-methylthiobenz(cd)indole hydriodide in ethanol solution, by the procedure of Example 52 yields the hydriodide of the title compound, convertible to the free base by treatment with hydroxide solution.

EXAMPLE 133

N-(3-(N-(3-(1H-imidazol-1-yl)propyl)-N-methyl)-propyl)benz(cd)indol-2-amine

The reaction of acrylonitrile and N-methyl-3-(1H-imidazol-1-yl)propanamine (Example 47) gives N-((3-(H-imidazol-1yl)propyl)-N-methylamino)propanecarbonitrile, which upon reduction with borane in tetrahydrofuran solution yields N-(3-(1H-imidazol-1yl) propyl)-N-methylpropane-1,3-diamine. Reaction of the latter compound with 2-methylthiobenz(cd)indol hydriodide in ethanol by the conditions of Example 52, followed by treatment with alkali hydroxide solution, yields the title compound.

EXAMPLE 134

N-(4-(5-Pyrimidinyl)butyl)benz(cd)indol-2-amine

The reaction of 4-(5-pyrimidinyl)butanamine and 2-methylthiobenz(cd)indole hydriodide in ethanol by the procedure of Example 52 gives a precipitate of the hydriodide salt, which is converted to the title compound by treatment with an alkali hydriodide solution.

EXAMPLE 135

N-(6-(3-Quinolinyl)hexyl)benz(cd)indol-2-amine

The reaction of 6-(3-quinolinyl)hexanamine and 2-methyl-thiobenz(cd)indole hydriodide in ethanol solution, by the procedure of Example 52, followed by treatment with alkali hydroxide solution, leads to the formation of the title compound.

EXAMPLE 136

N-(4-Pyridazinylmethyl)benz(cd)indol-2-amine

The reduction of 4-pyridazinecarbonamide by borane in dioxane solution leads to the formation of 4-pyridazinylmethylamine. Utilization of this amine in place of 2-pyridinylmethylamine by the method of Example 52 leads to the title compound.

EXAMPLE 137

N-(2-Pyrazinylmethyl)benz(cd)indol-2-amine

The borane reduction of 2-pyrazinecarbonamide in tetrahydrofuran solution yields 2-pyrazinemethylamine. The replacement of 2-pyridinemethylamine by this latter amine in the procedure of Example 52 leads to the title compound.

EXAMPLE 138

N-(3-(5-(2-Biphenylyl)-1,3,4-thiadiazol-2-yl)propyl)-benz(cd)indol-2-amine

A solution of 3-(5-(2-biphenylyl)-1,3,4-thiadiazol-2-yl)propanamine in ethanol is treated with 2-methylthiobenz(cd)indole hydriodide by the conditions of Example 52. Neutralization yields the title compound.

EXAMPLE 139

N-(5-(2,5-Dimethyl-(1H-pyrrol-1-yl)pentyl)benz(cd)indol-2-amine

The reaction of pentane-1,5-amine and 2,4-pentanedione (molar equivalents) leads to the formation of 5-(2,5-dimethyl-(1H-pyrrol-1yl))pentanamine as one of the isolable products. The reaction of the latter compound with molar equivalents of benz(cd) indol-2-thiol and mercuric acetate in refluxing ethanol, under the conditions of Example 55 leads to the formation of the title compound.

EXAMPLE 140

N-(3(1H-imidazol-1-yl)-2-methoxypropyl)benz(cd)indol-2-amine 1-(1H-imidazol-1yl)-3-(N-phthalimido) propan-2-ol, prepared as described in Example 74, is treated with sodium hydride in dimethylformamide solution, and methyliodide is then added, leading to the formation of the 2-methyoxy compound. This compound is then treated with hydrazine in refluxing ethanol solution yielding 3-(1H-imidazol-2-yl)-2-methoxypropanamine, which when reacted with 2-methylthiobenz(cd)indole hydriodide under the conditions of Example 52, yields the title compound.

EXAMPLE 141

N-(3-(1H-imidazol-1-yl)-2,2-spiro(pentamethylene)-propyl)benz(cd)indol-2-amine

Lithium aluminum hydride reduction of diethyl cyclohexane-1,1-dicarboxylate yields 1,1-bis(hydroxymethyl)cyclohexane, which on treatment with $PBr_3$ gives 1,1-bis(bromomethyl)cyclohexane. This compound upon sequential reactions with potassium phthalimide and then the sodium salt of imidazole leads to 1-(1H-imidazole-1-yl) methyl-1-(N-phthalimido)methylcyclohexane, which upon treatment with hydrazine in refluxing ethanol gives 1-(1H-imidazol-1yl) methylcylohexane-1-methylamine.

The reaction of the latter compound with 2-methylthio-benz(cd)indole hydriodide in ethanol by the procedure of Example 52, followed by neutralization with alkali hydroxide solution leads to the obtainment of the title compound.

EXAMPLE 142

1-Benz(cd)indol-2-aminomethyl-4-(1H-imidazol-1-ylmethyl)cyclohexane

Treatment of 1,4-cyclohexanedimethanol with $PBr_3$ yields 1,4-bis-(bromomethyl)cyclohexane. Subsequent sequential reactions with potassium phthalimide and then the sodium salt of imidazole gives 1-(1H-imidazol-1-yl) methyl-4-(N-phthalimido)methylcyclohexane. The action of hydrazine in refluxing ethanol on this latter compound leads to the formation of 4-(1H-imidazol-1yl)methylcyclohexane-1-methylamine.

The reaction of the amine and 2-methylthiobenz(cd)indole hydriodide in refluxing ethanol under the conditions of Example 52, followed by neutralization with alkali hydroxide solution gives the title compound.

EXAMPLE 143

(2,2-Difluoro-3-(1H-imidazol-1-yl)propyl)benz(cd)indol-2-amine

The sequential reaction of 1,3-dibromo-2,2-difluoropropane with potassium phthalimide and then the sodium salt of imidazole leads to the formation of N-(2,2-difluoro-3-(1H-imidazol-1-yl)propyl)phthalimide. Treatment of this compound with hydrazine in hot ethanol gives 2,2-difluoro-3-(1H-imidazol-1-yl)propanamine.

The reaction of the latter compound with 2-methylthiobenz(cd)indole hydriodide in refluxing ethanol, by the procedure of Example 52, followed by neutralization with alkali hydroxide solution, gives the title compound.

EXAMPLE 144

N-(1H-1,2,3-Triazol-1-yl) pentylbenz(cd)indol-2-amine

The reaction of the sodium salt of 1H-1,2,3-triazole and N-(5-bromopentyl)phthalimide gives N-(5-(1-H-1,2,3-triazol-1-yl)pentyl)phthalimide, which upon treatment with hydrazine in refluxing ethanol yields 5-(1H-1,2,3-triazol-1-yl)pentanamine.

Reaction of the latter compound and 2-methylthiobenz(cd)indole hydriodide in refluxing ethanol, by the procedure of Example 52, followed by neutralization with alkali hydroxide solutions gives the subject compound.

EXAMPLE 145

3-((1H-indol-1-yl) propyl)benz(cd)indol-2-amine

The addition of acrylonitrile to indole under basic catalysts yields 3-(1H-indol-1-yl)propanitrile, which, by reduction with borane in tetrahydrofuran, gives 3-(1H-indol-1-yl)propanamine.

The reaction of the latter compound and 2-methylthiobenz(cd)indole hydriodide in refluxing ethanol, followed by neutralization with alkali hydroxide solution, forms the title compound.

EXAMPLE 146

N-(3-(1-H-indazol-1-yl)propyl)benz(cd)indol-2-amine

The reaction of the sodium salt of indazole with N-(3-bromopropyl)phthalimide in dimethylformamide solution gives N-(3-(1H-indazol-1-yl)propyl)phthalimide, which upon treatment with hydrazine in refluxing ethanol leads to (3-(1H-indazol-1-yl)propanamine.

The action of 2-methylthiobenz(cd)indole hydriodide upon the latter compound, followed by neutralization with alkali hydroxide solution, under the conditions of Example 52, leads to the obtainment of the subject compound.

EXAMPLE 147

N-(4-(1H-Benzotriazol-1-yl) butyl)benz(cd)indol-2-amine

The reaction of N-(4-bromobutyl)phthalimide and the sodium salt of benzotriazole in dimethylformamide solution leads to the formation of N-(4-(1H-benzotriazol-1-yl)butyl)phthalimide, which is cleaved by hydrazine in refluxing ethanol to 4-(1H-benzo-triazol-1-yl)butanamine.

Under the procedure of Example 52, the latter compound and 2-methylthiobenz(cd)indole hydriodide react in hot ethanol solution to yield the hydriodide salt of the title compound, which is then obtained by neutralization with alkali hydroxide solution.

EXAMPLE 148

N-(Benz(cd)indol-2-yl)-N-(3-(1H-imidazol-1-yl)propyl)-3-pyridinecarbonamide

A solution of N-(3-(1H-imidazol-1-yl)propyl)benz(cd)indol-2-amine (the free base of the compound of Example 1) in pyridine is stirred as a molecular equivalent of 3-pyridinecarbonyl chloride hydrochloride is slowly added. The reaction mixture is then stirred at room temperature for 24 hours. The reaction mixture is then drowned onto ice, and the mixture basified to pH 9 with potassium carbonate solution. The precipitate is collected, washed with water, and dried. Recrystallization from dichloromethane-hexane then gives the pure title compound.

EXAMPLE 149

N-(4-(1H-imidazol-1yl)butyl)benz(cd)indol-2-amine

A 41.8 g portion of N-(4-(1H-imidazol-1-yl)butyl)-benz(cd)indol-2-amine, monohydroiodide was added to a stirred mixture of 500 ml of dichloromethane and 125 ml of 1N sodium hydroxide solution. After 1 hour the layers were separated and the dichloromethane layer dried over sodium sulfated. The sodium sulfate was filtered off and the filtrate evaporated to dryness in vacuo, giving 29 g of the desired compound as a bright orange yellow viscous oil.

EXAMPLE 150

N-(4-(1H-imidazol-1yl)butyl)benz(cd)indol-2-amine dihydrochloride

A solution of 12 g of N-(4-(1H-imidazol-1-yl)butyl)-benz(cd)indol-2-amine in 300 ml of dichloromethane was treated with 100 ml of 2N ethanolic hydrogen chloride. The solution was then taken to dryness in vacuo. The gummy residue was dissolved in 100 ml of water, treated with activated carbon, clarified and the filtrate taken to dryness in vacuo. The residue was treated with 200 ml of ethanol and then taken to dryness in vacuo. The evaporation from ethanol was repeated twice. The final residue was dried at 40° C. over $P_2O_5$ in vacuo, giving 18.4 g of the desired product as a hygroscopic golden foamy solid.

EXAMPLE 151

N-(4-(1H-imidazol-1yl)butyl)benz(cd)indole-2amine mono-and sesqui-butanedioic acid salts A solution of 5.3 g of N-(4-(1H-imidazol-1-yl)butyl)-benz(cd)indol-2-amine in 100 ml of acetone was added to a stirred, boiling solution of 2.1 g (1molar equivalent) of butanedioic acid (succinic acid) in 150 ml of acetone. A tacky precipitate formed. The acetone was decanted and the precipitate recrystallized with cooling from 150 ml of ethanol, giving 5.1 g of the monobutanedioic acid salt, m.p. 139°-140° C.

a solution of 5.1 g of N-(4-(1H-imidazol-1-yl)butyl)-benz(cd)indol-2-amine in 100 ml of hot ethanol was added to a stirred boiling solution of 5.1 g (2.5 molar equivalents) of butanedioic acid in 150 ml of ethanol. The resultant solution was concentrated to 200 ml and cooled to −10° C. The precipitate was collected and dried, giving 3.3 g of the sesquibutanedioic acid salt, m.p. 124°-126° C.

EXAMPLE 152

N-(4-(1H-imidazol-1-yl)butyl)benz(cd)indole-2-amine bis- and sesqui-(E)-2-butenedioic acid salts A solution of 6.8 g of N-(4-(1H-imidazol-1-yl)butyl)-benz(cd)indol-2-amine in 135 ml of acetone was added dropwise to a stirred, boiling solution of 6.0 g (2.2 molar equivalents) of (E)-2-butenedioic acid (fumaric acid)in 1200 ml of acetone. After stirring at room temperature for 15 minutes, the bright yellow precipitate was collected, washed with acetone and dried, giving 10.8 g of the bis-(E)-2-butenedioic acid salt, m.p. 161°-163° C.

A 5.0 g portion of the above bis-salt was recrystallized from 500 ml of ethanol, giving 3.8 g of the sesqui-(E)-2-butenedioic acid salt, m.p. 165°-167° C. (decomposition).

EXAMPLE 153

N-(4-(1H-imidazol-2-yl)butyl)benz(cd)indole-2-amine, bis-(R-(R*,R*))-2,3-dihydroxybutanedioic acid salt A solution of 6.7 g of N-(4-(1H-imidazol-1yl)butyl)-benz(cd)indol-2-amine in 24 ml of ethanol was added to a stirred, boiling solution of 7.0 g (2molar equivalents of (R-(R*,R*))-2,3-dihydroxybutanedioic acid (L-tartaric acid) in 500 ml of ethanol. After stirring at room temperature for 1 hour, the yellow precipitate was collected and dried, giving 1.6 g of bis-(R-(R*,R*)-2,3-dihydroxybutanedioic acid salt, m.p. 75°-80° C.

EXAMPLE 154

N-(4-(1H-imidazol-1yl)butyl)benz(cd)indol-2-amine bis-(Z)-2-butenedioic acid salt A solution of 6.4 g of N-(4-(1H-imidazol-1-yl)butyl)-benz(cd)indol-2-amine in 100 ml of acetone was added to a stirred, boiling solution of 6.2 g (2.4 molar equivalents) of (Z)-2-butenedioic acid (maleic acid) in 100 ml of acetone. A reddish oil precipitated out. Ethanol was added until solution occurred, then diethyl ether was added until turbidity was produced. Cooling at −10° a tacky precipitate. The supernatant solution was clarified and left at −10° C. Scratching induced the formation of a yellow precipitate which was collected and dried giving the hygroscopic bis-(Z)-2-butenedioic acid salt, m.p. 75°–80° C.

EXAMPLE 155

N-(3-(1H-indazol-1-yl)propyl)benz(cd) indol-2-amine formate

N-(3-Aminopropyl)indazole was prepared as follows: the sodium salt of indazole and N-(3-bromopropylphthalimide) were combined in dimethylformamide solution and heated on a steam bath to yield N-(3-phthalimidopropyl)indazole. Deblocking with hydrazine in refluxing ethanol solution gave the desired intermediate.

A solution of 5.4 grams of N-(3-aminopropyl)indazole in 400 ml of ethanol was treated with 6.0 grams of benz(cd)indole-2-thione and then 11.0 grams of mercuric acetate. The mixture was then stirred under reflux for 8 hours. The black slurry was cooled to room temperature and treated with 7.5 ml of 10N sodium hydroxide. The reaction was filtered through a bed of celite, and the filtrate then concentrated to dryness in vacuo. The residue was partitioned between 250 ml of dichloromethane and 150 ml of water. The dichloromethane layer was concentrated to dryness. The residue was dissolved in 200 ml of acetone and the solution added to a stirred boiling solution of 6.0 grams of fumaric acid in 1200 ml of acetone. A precipitate formed at once. The reaction mixture was stirred at room temperature for two hours, the precipitate collected and dried. It melted at 163°–165° C. with decomposition.

Analysis:

Calculated for: $C_{21}H_{18}N_4C_4H_4O_4$: C, 67.86; H, 5.01; N, 1266;

Found: C, 67.39; H, 5.01; N, 12.65.

EXAMPLE 156

2-(Benz(cd)indol-2-ylamino)-N-(3-pyridinylmethylacetamide and sesqui fumaric acid salt A solution of 3.3 grams of 2-amino-N-(3-pyridinylmethyl)acetamide in 100 ml of ethanol was stirred as 6.0 grams of 2-methylthiobenz(cd)indole hydriodide was added. The mixture was stirred under reflux for 16 hours, cooled at −10° C. and then diluted with 100 ml of ether and stored at −10° C. The resultant precipitate was collected and shaken with 2 ml of 10N odium hydroxide solution. The mixture was extracted with two portions of 350 ml each of methylene chloride. Removal of the methylene chloride in vacuo and recrystallization from 200 ml of acetone gave the free base as a yellow solid melting at 195°–200° C. with decomposition.

Analysis:

Calculated for $C_{19}H_{16}N_4O$: C, 72.13; H, 5.10; N, 17.71.

Found: C, 71.74; H, 5.14; N, 17.79.

The mother liquors from the above preparation were treated with a boiling solution of 4.5 grams of fumaric acid in 1200 ml of acetone. The combined solutions were concentrated to 800 ml and cooled at −10° C. The sesqui fumaric acid salt precipitated as a yellow powder, melting at 161°–164° C. with decomposition.

Analysis:

Calculated for $C_{19}H_{16}N_4O.1.5C_4H_4O_4$: C, 61.22; H, 4.52; N, 11.42.

Found: C, 61.89; H, 4.68; N, 11.47.

The starting amine, 2-amine-N-(3-pyridinylmethyl) acetamide, was prepared as follows: the reaction of 3-pyridinylmethylamine and N-carbobenzyloxyglycine via the usual peptide synthesis procedure gave 2-carbobenzyloxyamino-N-(3-prydinylmethyl)acetamide which upon deblocking gave the desired intermediate.

EXAMPLE 157

N-(4-Pyrazinylbutyl)benz(cd)indol-2-amine fumarate

A mixture consisting of 1.13 grams of 4-pyrazinylbutylamine, 1.4 benz(cd)indol-2-(1H)-thione, 2.4 grams of mercuric acetate, and 110 ml of ethane was stirred and heated under reflux for 6 hours. The hot reaction mixture was filtered through diatomaceous earth, the filtrate taken to dryness in vacuo, and the resultant residue partitioned between 100 ml of chloroform and 100 ml of 1N sodium hydroxide. The chloroform layer was dried and taken to dryness in vacuo, giving 2.3 grams of viscous oil. This was taken up in 25 ml of hot ethanol and added to a hot solution of 1.05 grams of fumaric acid in 10 ml of ethanol. Cooling at 0° C. gave 2.2 g of N-(4-pyrazinylbutyl)benz(cd) indol-2-amine fumarate; m.p. 185°–186° C.

Analysis:

Calculated for $C_{19}H_{18}N_4.C_4H_4O_4$: C, 66.02; H, 5.30; N, 13.39.

Found: C, 65.48; H, 5.24; N, 13.24

The above-identified patents, references, examples and test methods are incorporated herein by reference.

Many variations of this invention will suggest themselves to those skilled in this art in light of the above, detailed description. All such obvious modifications are within the full intended scope of the appended claims.

What is claimed is:

1. A compound of the formula:

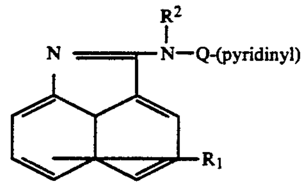

wherein: $R_1$ is one or more of bromo, chloro, fluoro, iodo, loweralkyloxy, loweralkylthio, loweralkylsulfonyl, arylsulfonyl, hydroxy, mercapto, loweralkylcarbonyloxy, amino, mono(loweralkyl)amino, di(loweralkyl)amino, (alpha,omega-alkylene)amino, loweralkyl, aryl(loweralkyl), cycloalkyl, lowercycloalkyloxy, loweralkylcarbonyl, arylcarbonyl, cyano, sulfonamido, N-(loweralkyl)sulfonamido, N,N-(diloweralkyl)sulfonamido, alpha-hydroxy(lower)alkyl, alpha-amino(-loweralkyl), alpha-(loweralkyl)amino- (loweralkyl), alpha-(diloweralkyl) amino(loweralkyl), carboxamido, N-(loweralkyl) carboxamido, or N,N-(diloweralkyl)-carboxamido, the remaining positions in the naphthalene ring being hydrogen; $R_2$ is hydrogen, alkyl, aryl, arylalkyl, cycloalkyl, alkyl ($C_1$-$C_6$)carbonyl, (substituted aryl) carbonyl, furancarbonyl, thiophencarbonyl, pyridine-carbonyl, arylsulfonyl or arylaminocarbonyl; Q is $(CH_2)_n$ where n is an integer from 1 to 12, where such chain is substituted by one or more lower alkyl, cycloalkyl, arylalkyl, aryl, lower spiroalkyl, hydroxy, loweralkoxy, fluoro, where such chain contains one or more—($C_2$-$C_8$)—CH═CH—or —($C_2$-$C_8$)—C≡C—linkages, where the chain may also be cyclohexane(bisalkyl), where such chain may have functions such as —O—, —S—, —$SO_2$—, —NH—,

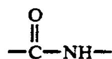

(where $R_3$ is hydrogen, alkyl, aryl, arylalkyl, or cycloalkyl), or $$-\overset{\overset{\displaystyle O}{\|}}{C}-NH-$$

replacing one of the —$CH_2$—groups; and the pharmacologically acceptable salts thereof; wherein lower alkyl denotes a group comprises of 1–8 carbon atoms; alkyl denotes a group comprised of 1–30 carbon atoms; arylalkyl denotes a group comprised of 7–21 carbon atoms; alkylene denotes a group comprised of 2–8 carbon atoms; cycloalkyl denotes a group comprised of 3–10 carbon atoms; alkoxy denotes an alkyl ether group in which the alkyl group comprises of 1–30 carbon atoms; lower alkoxy denotes an alkyl ether group in which lower alkyl group comprises 1–8 carbon atoms; aryl denotes a group comprising a monocarbocyclic group, or a dicarbocyclic group or a tricarbocyclic group or aryl groups having substituents comprising the following: hydrogen, halogen, trifluoromethyl, cyano, carboxy, amino, alkyl having from one to four carbon atoms, alkoxy having from one to four carbon atoms, benzylamino, allylamino, alkylamine having from one to three carbon atoms, dialkylamino having from one to three carbon atoms in each alkyl group, alkylthio having from one to three carbon atoms, alkylsulfonyl having from one to three carbon atoms; acetyl, acetamido, phenyl and benzoyl; and halogen denotes bromine, chlorine, fluorine or iodine, or a mixture of any of the foregoing.

2. The compound according to claim 1, N-(3-(3-pyridinyl)propyl)benz(cd)indol-2-amine fumarate.

3. The compound according to claim 1, N-(3-(3-pyridinyloxy)propyl)benz(cd)indol-2-amine fumarate.

4. The compound according to claim 1, 6-bromo-N-(4-(3-pyridinyl)butyl)benz(cd)indol-2-amine sesquifumarate.

5. The compound according to claim 1, N-(4-(3-pyridinyl)butyl)benz(cd)indol-2-amine, hydriodide salt.

6. The compound according to claim 1, N-(4-(3-pyridinyl)butyl)benz(cd)indol-2-amine, sesqui-fumarate salt.

7. The compound according to claim 1, N-(2-(3-pyridinyl)ethyl)benz(cd)indol-2-amine sesqui-fumarate.

8. A method of inhibiting thromboxane synthetase enzyme in a mammal which comprises administering internally to said mammal a thromboxane synthetase enzyme inhibiting amount of a compound of claim 1.

9. A thromboxane synthetase enzyme inhibiting composition of matter in dosage unit form comprising from about 10 mg to about 700 mg of a compound of claim 1 in association with a pharmacologically acceptable carrier.

10. A method of inhibiting hypertension in a mammal which comprises administering to said mammal a hypotensive amount of a compound of claim 1.

11. A method of inhibiting arrhythmia in a mammal which comprises administering internally to said mammal an arrhythmia inhibiting amount of a compound of claim 1.

12. A method for blocking alpha-adrenoceptors on heart muscle in a mammal which comprises administering internally to a mammal an alpha-adrenoceptor blocking amount of a compound of claim 1.

* * * * *